United States Patent
Dall'Occo et al.

(10) Patent No.: US 6,864,333 B2
(45) Date of Patent: Mar. 8, 2005

(54) PROCESS FOR THE PREPARATION OF ETHYLENE POLYMERS

(75) Inventors: Tiziano Dall'Occo, Ferrara (IT); Ofelia Fusco, Ferrara (IT); Ilya E. Nifant'ev, Moscow (RU); Ilya P. Laishevtsev, Moscow (RU)

(73) Assignee: Basel Polyolefine GmbH, Wesseling (DE)

( * ) Notice: Subject to any disclaimer, the term of this patent is extended or adjusted under 35 U.S.C. 154(b) by 0 days.

(21) Appl. No.: 09/914,305

(22) PCT Filed: Dec. 22, 2000

(86) PCT No.: PCT/EP00/13192

§ 371 (c)(1),
(2), (4) Date: Aug. 27, 2001

(87) PCT Pub. No.: WO01/48039

PCT Pub. Date: Jul. 5, 2001

(65) Prior Publication Data

US 2002/0198339 A1 Dec. 26, 2002

(30) Foreign Application Priority Data

Dec. 28, 1999 (EP) .............................. 99204566

(51) Int. Cl.$^7$ ................................. C08F 4/52
(52) U.S. Cl. ..................... 526/161; 526/172; 526/134; 526/348; 556/53
(58) Field of Search ................ 526/143, 165, 526/160, 161, 172, 134; 502/117; 556/51, 53

(56) References Cited

U.S. PATENT DOCUMENTS 5,198,401 A * 3/1993 Turner et al. .............. 502/155
5,948,873 A * 9/1999 Santi et al. ................. 526/129
2003/0036610 A1 * 2/2003 Fusco et al. .................. 526/90
2003/0036612 A1 * 2/2003 Nifant'ev et al. ........... 526/160

FOREIGN PATENT DOCUMENTS

| EP | 0399348 | 11/1990 | ........... C08F/10/02 |
| EP | 0633272 | 1/1995 | ........... C08F/10/02 |
| WO | 9200333 | 1/1992 | ............. C08F/4/76 |
| WO | 9526369 | 10/1995 | ........... C08F/10/00 |
| WO | 9532995 | 12/1995 | ........... C08F/10/00 |
| WO | WO 98/22486 * | 5/1998 | ........... C07F/17/00 |
| WO | WO 98/22486 A1 * | 5/1998 | ........... C07F/17/00 |
| WO | 9822486 | 5/1998 | ........... C07F/17/00 |
| WO | 9921899 | 5/1999 | ........... C08F/10/02 |
| WO | 0121674 | 3/2001 | ........... C08F/10/00 |

OTHER PUBLICATIONS

Ewen, et al. J. Am. Chem. Soc. 1998, 120, 10786.*
Kraak et al. Tetrahedron 1968, 24, 3381.*
Iyoda, et al. Tetrahedron Letters 1997, 38(26), 4581.*
Elschenbroich, C.; Salzer A. Organometallics VCH: New York, 1989, pp. 19–29.*
C. J. Carman et al., Macromolecules, 10: 536–544 (1977).
J. Randall, Macromol. Chem. Phys., 29: 201–317 (1989).
T. Uozumi et al., Mak. Chemic., 193(4): 823–831 (1992).
E. Hey–Hawkins, Chem. Rev., 94: 1661–1717 (1994).
J. Ewen et al., J. Am. Chem. Soc., 120: 10786–10787 (1998).

* cited by examiner

Primary Examiner—David W. Wu
Assistant Examiner—Rip A. Lee

(57) ABSTRACT

Ethylene based polymers having high molecular weights can be obtained in high yields at temperatures of industrial interest, by carrying out the polymerization reaction in the presence of catalysts comprising single carbon bridged metallocenes, which has a particular ligand system containing a heteroatom.

20 Claims, No Drawings

PROCESS FOR THE PREPARATION OF ETHYLENE POLYMERS

This application is a U.S. National Stage of International Application PCT/EP00/13192, filed Dec. 22, 2000.

The present invention relates to a polymerization process for the preparation of ethylene polymers in the presence of a metallocene catalyst. The invention also relates to a process for preparing the corresponding ligands which are useful as intermediates in the synthesis of said metallocene compounds.

Metallocene compounds having two bridged cyclopentadienyl groups are known as catalyst components for the homo- and copolymerization reaction of ethylene.

For example, EP-A-0 399 348 discloses the polymerization of ethylene in the presence of indenyl based metallocenes. Although the polyethylene obtained has industrially acceptable molecular weight, the metallocene used in the polymerization process has low polymerization activity.

More recently, heterocyclic metallocene compounds used in the polymerization of alpha-olefins have been described.

In International application WO 98/22486 it is disclosed a class of metallocenes containing a cyclopentadienyl radical directly coordinating the central metal atom, to which are fused one or more rings containing at least one heteroatom. These metallocenes, in combination with a suitable cocatatlyst, are used in the polymerization of olefins such as ethylene. However, the molecular weights that can be obtained at polymerization temperatures of industrial interest are still too low for many applications and the activity of these catalyst systems, when used in the polymerization of ethylene, is not satisfactory.

It would be desirable to identify metallocenes which, when used in catalysts for the polymerization of ethylene, have high activity, such that the amount of the catalyst remaining in the polymer is minimized, and which are capable of yielding polymers endowed with high molecular weights.

It has been unexpectedly found that it is possible to prepare ethylene polymers having high molecular weights with high yields, operating at temperatures of industrial interest, by carrying out the polymerization reaction of ethylene in the presence of a catalyst based on a class of heteroatom containing metallocene compounds.

Thus, according to a first aspect of the present invention, a process is provided for the preparation of ethylene polymers comprising the polymerization reaction of ethylene and optionally one or more olefins in the presence of a catalyst comprising the product obtainable by contacting:
(A) metallocene compound of formula (I):

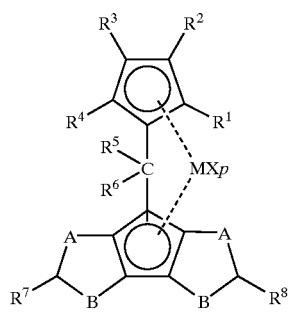

(I)

wherein the rings containing A and B have a double bond in the allowed position having an aromatic character;

A and B are selected from sulfur (S), oxygen (O) and $CR^9$, $R^9$ being selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms belonging to groups 13 or 15–17 of the Periodic Table of the Elements, with the proviso that if A is S or O, B is $CR^9$ or if B is S or O, A is $CR^9$, i.e. either A or B being different from $CR^9$; $R^1$, $R^2$, $R^3$, $R^4$, $R^5$, $R^6$, $R^7$, and $R^8$ which may be the same as or different from each other, are selected from hydrogen, a $C_1$–$C_{20}$-alkyl, $C_3$–$C_{20}$-cycloalkyl, $C_2$–$_{20}$-alkenyl, $C_6$–$C_{20}$-aryl, $C_7$–$C_{20}$-alkylaryl, $C_7$–$C_{20}$-arylalkyl radical, optionally containing heteroatoms belonging to groups 13 or 15–17 of the Periodic Table of the Elements, and two adjacent $R^1$ and $R^2$ and/or $R^3$ and $R^4$ and/or $R^5$ and $R^6$ can form a ring comprising 4 to 8 atoms, which can bear substituents;

preferably at least one of $R^1$, $R^2$, $R^3$, $R^4$, $R^7$ and $R^8$ is not hydrogen;

M is an atom of a transition metal selected from those belonging to group 3, 4, 5, 6 or to the lanthamide or actinide groups in the Periodic Table of the Elements (new IUPAC version), X, which may be the same as or different from each other, is hydrogen, a halogen atom, or a group $R^{10}$, $OR^{10}$, $OSO_2CF_3$, $OCOR^{10}$, $SR^{10}$, $NR^{10}_2$ or $PR^{10}_2$, wherein the substituents $R^{10}$ are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms belonging to groups 13 or 15–17 of the Periodic Table of the Elements;

p is an integer of fin 0 to 3, preferably from 1 to 3 being equal to the oxidation state of the metal M minus 2;

isopropylidene(cyclopentadienyl)-7-(cyclopentadienyl-[1,2-b:4,3-b']-dithiophene)zirconium dichloride being excluded;

and (B) an alumoxane and/or a compound capable of forming an alkyl metallocene cation.

The transition metal M is preferably selected form titanium, zirconium and hafnium preferably having formal oxidation state of +4. Most preferably, the transition metal M is zirconium.

The X substituents are preferably chlorine atoms or methyl groups. Most preferably X are chlorine atoms.

Preferably A and B are selected from sulfur and a CH group, either A or B being different from CH; $R^5$ and $R^6$ are $C_1$–$C_{20}$-alkyl groups, such as methyl, and $R^7$ is equal to $R^8$; preferably $R^1$, $R^3$ and $R^4$ are hydrogen.

Preferably, $R^2$ is hydrogen or $C_1$–$C_{20}$-alkyl groups such as methyl or tert-butyl, and $R^7$ and $R^8$ are hydrogen or methyl groups even more preferably $R^2$ is $C_1$–$C_{20}$-alkyl groups.

A further object of the present invention is a metallocene compound of formula (I)

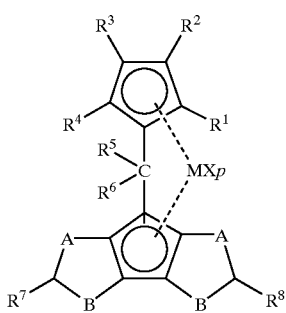

(I)

wherein A, B, M, X, p, R¹, R², R³, R⁴, R⁵, R⁶, R⁷, R⁸, and R⁹ are above described;
isopropylidene(cyclopentadienyl)-7-(cyclopentadithophene)zirconium dichloride,
isopropylidene(3-methyl-cyclopentadienyl)-7-(cyclopentadithiophene)zirconium dichloride;
isopropylidene(3-ethyl-cyclopentadienyl)-7-(cyclopentadithiophene)zirconium dichloride;
isopropylidene(3-t-butyl-cyclopentadienyl)-7-(cyclopentadithiophene)zirconium dichloride;
isopropylidene(3-n-butyl-cyclopentadienyl)-7-(cyclopentadithiophene)zirconium dichloride;
isopropylidene(3-trimethysilyl-cyclopentadienyl)-7-(cyclopentadithiophene)zirconium dichloride and
isopropylidene (3-i-propylcyclopentadienyl)-7-(cyclopentadithiophene)zirconium dichloride being excluded.

Non-limiting examples of metallocene compounds suitable for use in the process of the invention are:
methylene(3-trimethylsilyl-cyclopentadienyl)-7-(cyclopentadienyl-[1,2-b:4,3-b']dithiophene)zirconium dichloride and dimethyl;
methylene(cyclopentadienyl)-7-(2,5-ditrimethylsilyl-cyclopentadienyl-[1,2-b:4,3-b']dithiophene)zirconium dichloride and dimethyl;
methylene(3-trimethylsilyl-cyclopentadienyl)-7-(2,5-ditrimethylsilyl-cyclopentadienyl-[1,2-b:4,3-b']dithiophene)zirconium dichloride and dimethyl;
methylene(3-methyl-cyclopentadienyl)-7-(cyclopentadienyl-[1,2-b:4,3-b']dithiophene)zirconium dichloride and dimethyl;
methylene(3-methyl-cyclopentadienyl)-7-(cyclopentadienyl-[1,2-b:4,3-b']dioxazole)zirconium dichloride and dimethyl;
methylene(cyclopentadienyl)-7-(2,5-dimethylphosphinocyclopentadienyl-[1,2-b:4,3-b']dithiophene)zirconium dichloride and dimethyl;
methylene(cyclopentadienyl)-7-(2,5-dimethylphosphinocyclopentadienyl-[1,2-b:4,3-b']dioxazole)zirconium dichloride and dimethyl;
methylene(cyclopentadienyl)-7-(2,5-diphenylylphosphinocyclopentadienyl-[1,2-b:4,3-b']dithiophene)zirconium dichloride and dimethyl;
methylene(cyclopentadienyl)-7-(2,5-dimethoxyphosphinocyclopentadienyl-[1,2-b:4,3-b']dithiophene)zirconium dichloride and dimethyl;
methylene(cyclopentadienyl)-7-(2,5-dimethoxyborylcyclopentadienyl-[1,2-b:4,3-b']dithiophene)zirconium dichloride and dimethyl;
methylene(cyclopentadienyl)-7-(2,5-dimethoxycyclopentadienyl-[1,2-b:4,3-b']dithiophene)zirconium dichloride and dimethyl;
methylene(3-methoxycyclopentadienyl)-7-(2,5-dimethoxycyclopentadienyl-[1,2-b:4,3-b']dithiophene)zirconium dichloride and dimethyl;
methylene(cyclopentadienyl)-7-(2,5-dithiocyclopentadienyl-[1,2-b:4,3-b']dithiophene)zirconium dichloride and dimethyl;
methylene(3-methyl-cyclopentadienyl)-7-(cyclopentadienyl-[1,2-b:4,3-b']dithiophene)zirconium dichloride and dimethyl;
methylene(3-ethyl-cyclopentadienyl)-7-(cyclopentadienyl-[1,2-b:4,3-b']dithiophene)zirconium dichloride and dimethyl;
methylene(3-isopropyl-cyclopentadienyl)-7-(cyclopentadienyl-[1,2-b:4,3-b']dithiophene)zirconium dichloride and dimethyl;
methylene(3-tert-butyl-cyclopentadienyl)-7-(cyclopentadienyl-[1,2-b:4,3-b']dithiophene)zirconium dichloride and dimethyl;
methylene(3-phenyl-cyclopentadienyl)-7-(cyclopentadienyl-[1,2-b:4,3-b']dithiophene)zirconium dichloride and dimethyl;
methylene(2,3-dimethyl-cyclopentadienyl)-7-(cyclopentadienyl-[1,2-b:4,3-b']dithiophene)zirconium dichloride and dimethyl;
methylene(2,3-diethyl-cyclopentadienyl)-7-(cyclopentadienyl-[1,2-b:4,3-b']dithiophene)zirconium dichloride and dimethyl;
methylene(2,3-diisopropyl-cyclopentadienyl)-7-(cyclopentadienyl-[1,2-b:4,3-b']dithiophene)zirconium dichloride and dimethyl;
methylene(2,3-ditert-butyl-cyclopentadienyl)-7-(cyclopentadienyl-[1,2-b:4,3-b']dithiopbene)zirconium dichloride and dimethyl;
methylene(2,3,5-trimethyl-cyclopentadienyl)-7-(cyclopentadienyl-[1,2-b:4,3-b']dithiophene)zirconium dichloride and dimethyl;
methylene(2,3,5-triethyl-cyclopentadienyl)-7-(cyclopentadienyl-[1,2-b:4,3-b']dithiophene)zirconium dichloride and dimethyl;
methylene(2,3,5-triisopropyl-cyclopentadienyl)-7-(cyclopentadienyl-[1,2-b:4,3-b']dithiophene)zirconium dichloride and dimethyl;
methylene(2,3,5-tritert-butyl-cyclopentadienyl)-7-(cyclopentadienyl-[1,2-b:4,3-b']dithiophene)zirconium dichloride and dimethyl;
methylene(2,3,4,5-tetramethyl-cyclopentadienyl)-7-(cyclopentadienyl-[1,2-b:4,3-b']dithiophene)zirconium dichloride and dimethyl;
methylene(2,3,4,5-tetraethyl-cyclopentadienyl)-7-(cyclopentadienyl-[1,2-b:4,3-b']dithiophene)zirconium dichloride and dimethyl;
methylene(2,3,4,5-tetraisopropyl-cyclopentadienyl)-7-(cyclopentadienyl-[1,2-b:4,3-b']dithiophene)zirconium dichloride and dimethyl;
isopropylidene(3-trimethylsilyl-cyclopentadienyl)-7-(cyclopentadienyl-[1,2-b:4,3-b']dithiophene)zirconium dichloride and dimethyl;
isopropylidene(cyclopentadienyl)-7-(2,5-ditrimethylsilyl-cyclopentadienyl-[1,2-b:4,3-b']dithiophene)zirconium dichloride and dimethyl;
isopropylidene(cyclopentadienyl)-7-(2,5-ditrimethylsilyl-cyclopentadienyl-[1,2-b:4,3-b']dioxazole)zirconium dichloride and dimethyl;
isopropylidene(3-trimethylsilyl-cyclopentadienyl)-7-(2,5-ditrimethylsilyl-cyclopentadienyl-[1,2-b:4,3-b']-dithiophene)zirconium dichloride and dimethyl;
isopropylidene(cyclopentadienyl)-7-(2,5-dimethylphosphinocyclopentadienyl-[1,2-b:4,3-b']dithiophene)zirconium dichloride and dimethyl;
isopropylidene(cyclopentadienyl)-7-(2,5-dimethylphosphinocyclopentadienyl-[1,2-b:4,3-b']dioxazole)zirconium dichloride and dimethyl;

isopropylidene(cyclopendienyl)-7-(2,5-diphenylylphosphinocyclopentadienyl-[1,2-b:4,3-b']dithiophene)zirconium dichloride and dimethyl;

isopropylidene(cyclopentadienyl)-7-(2,5-dimethoxyphosphinocyclopentadienyl-[1,2-b:4,3-b']dithiophene)zirconium dichloride and dimethyl;

isopropylidene(cyclopentadienyl)-7-(2,5-dimethoxyborylcyclopentadienyl-[1,2-b:4,3-b']dithiophene)zirconium dichloride and dimethyl;

isopropylidene(cyclopentadienyl)-7-(2,5-dimethoxycyclopentadienyl-[1,2-b:4,3-b']dithiophene)zirconium dichloride and dimethyl;

isopropylidene(3-methoxycyclopentadienyl)-7-(2,5-dimethoxycyclopentadienyl-[1,2-b:4,3-b']dithiophene)zirconium dichloride and dimethyl;

isopropylidene(cyclopentadienyl)-7-(2,5-dithiocyclopentadienyl-[1,2-b:4,3-b']dithiophene)zirconium dichloride and dimethyl;

isopropylidene(3-methyl-cyclopentadienyl)-7-(cyclopentadienyl-[1,2-b:4,3-b']dithiophene)zirconium dichloride and dimethyl;

isopropylidene(3-ethyl-cyclopentadienyl)-7-(cyclopentadienyl-[1,2-b:4,3-b']dithiophene)zirconium dichloride and dimethyl;

isopropylidene(3-isopropyl-cyclopentadienyl)-7-(cyclopentadienyl-[1,2-b:4,3-b']dithiophene)zirconium dichloride and dimethyl;

isopropylidene(3-tert-butyl-cyclopentadienyl)-7-(cyclopentadienyl-[1,2-b:4,3-b']dithiophene)zirconium dichloride and dimethyl;

isopropylidene(3-phenyl-cyclopentadienyl)-7-(cyclopentadienyl-[1,2-b:4,3-b']dithiophene)zirconium dichloride and dimethyl;

isopropylidene(2,3-dimethyl-cyclopentadienyl)-7-(cyclopentadienyl-[1,2-b:4,3-b']dithiophene)zirconium dichloride and dimethyl;

isopropylidene(2,3-diethyl-cyclopentadienyl)-7-(cyclopentadienyl-[1,2-b:4,3-b']dithiophene)zirconium dichloride and dimethyl;

isopropylidene(2,3-diisopropyl-cyclopentadienyl)-7-(cyclopentadienyl-[1,2-b:4,3-b']dithiophene)zirconium dichloride and dimethyl;

isopropylidene(2,3-ditert-butyl-cyclopentadienyl)-7-(cyclopentadienyl-[1,2-b:4,3-b']dithiophene)zirconium dichloride and dimethyl;

isopropylidene(2,3,5-trimethyl-cyclopentadienyl)-7-(cyclopentadienyl-[1,2-b:4,3-b']dithiophene)zirconium dichloride and dimethyl;

isopropylidene(2,3,5-triethyl-cyclopentadienyl)-7-(cyclopentadienyl-[1,2-b:4,3-b']dithiophene)zirconium dichloride and dimethyl;

isopropylidene(2,3,5-triisopropyl-cyclopentadienyl)-7-(cyclopentadienyl-[1,2-b:4,3-b']dithiophene)zirconium dichloride and dimethyl;

isopropylidene(2,3,5-tritert-butyl-cyclopentadienyl)-7-(cyclopentadienyl-[1,2-b:4,3-b']dithiophene)zirconium dichloride and dimethyl;

isopropylidene(2,3,4,5-tetramethyl-cyclopentadienyl)-7-(cyclopentadienyl-[1,2-b:4,3-b']dithiophene)zirconium dichloride and dimethyl;

isopropylidene(2,3,4,5-tetraethyl-cyclopentadienyl)-7-(cyclopentadienyl-[1,2-b:4,3-b']dithiophene)zirconium dichloride and dimethyl;

isopropylidene(2,3,4,5-tetraisopropyl-cyclopentadienyl)-7-(cyclopentadienyl-[1,2-b:4,3-b']dithiophene)zirconium dichloride and dimethyl;

methylene(3-trimethylsilyl-cyclopentadienyl)-7-(2,5-dimethyl-cyclopentadienyl-[1,2-b:4,3-b']-dithiophene)zirconium dichloride and dimethyl;

methylene(3-methyl-cyclopentadienyl)-7-(2,5-dimethyl-cyclopentadienyl-[1,2-b:4,3-b']-dithiophene)zirconium dichloride and dimethyl;

methylene(3-methyl-cyclopentadienyl)-7-(2,5-ditrimethylsilyl-cyclopentadienyl-[1,2-b:4,3-b']-dithiophene)zirconium dichloride and dimethyl;

methylene(3-ethyl-cyclopentadienyl)-7-(2,5-dimethyl-cyclopentadienyl-[1,2-b:4,3-b']dithiophene)zirconium dichloride and dimethyl;

methylene(3-isopropyl-cyclopentadienyl)-7-(2,5-dimethyl-cyclopentadienyl-[1,2-b:4,3-b']-dithiophene)zirconium dichloride and dimethyl; methylene(3-isopropyl-cyclopentadienyl)-7-(2,5-ditrimethylsilyl-cyclopentadienyl-[1,2-b:4,3-b']-dithiophene)zirconium dichloride and dimethyl;

methylene(3-tert-butyl-cyclopentadienyl)-7-(2,5-dimethyl-cyclopentadienyl-[1,2-b:4,3-b']-dithiophene)zirconium dichloride and dimethyl;

methylene(3-phenyl-cyclopentadienyl)-7-(2,5-dimethyl-cyclopentadienyl-[1,2-b:4,3-b']-dithiophene)zirconium dichloride and dimethyl;

methylene(3-phenyl-cyclopentadienyl)-7-(2,5-ditrimethylsilyl-cyclopentadienyl-[1,2-b:4,3-b']-dithiophene)zirconium dichloride and dimethyl;

methylene(2,3-dimethyl-cyclopentadienyl)-7-(2,5-dimethyl-cyclopentadienyl-[1,2-b:4,3-b']-dithiophene)zirconium dichloride and dimethyl;

methylene(2,3-diethyl-cyclopentadienyl)-7-(2,5-dimethyl-cyclopentadienyl-[1,2-b:4,3-b']-dithiophene)zirconium dichloride and dimethyl;

methylene(2,3-diisopropyl-cyclopentadienyl)-7-(2,5-dimethyl-cyclopentadienyl-[1,2-b:4,3-b']-dithiophene)zirconium dichloride and dimethyl;

methylene(2,3-ditert-butyl-cyclopentadienyl)-7-(2,5-dimethyl-cyclopentadienyl-[1,2-b:4,3-b']-dithiophene)zirconium dichloride and dimethyl;

methylene(2,3,5-trimethyl-cyclopentadienyl)-7-(2,5-dimethyl-cyclopentadienyl-[1,2-b:4,3-b']-dithiophene)zirconium dichloride and dimethyl;

methylene(2,3,5-triethyl-cyclopentadienyl)-7-(2,5-dimethyl-cyclopentadienyl-[1,2-b:4,3-b']-dithiophene)zirconium dichloride and dimethyl;

methylene(2,3,5-triisopropyl-cyclopentadienyl)-7-(2,5-dimethyl-cyclopentadienyl-[1,2-b:4,3-b']-dithiophene)zirconium dichloride and dimethyl;

methylene(2,3,5-tritert-butyl-cyclopentadienyl)-7-(2,5-dimethyl-cyclopentadienyl-[1,2-b :4,3-b']-dithiophene)zirconium dichloride and dimethyl;

methylene(2,3,4,5-tetramethyl-cyclopentadienyl)-7-(2,5-dimethyl-cyclopentadienyl-[1,2-b:4,3-b']-dithiophene)zirconium dichloride and dimethyl;

methylene(2,3,4,5-tetraethyl-cyclopentadienyl)-7-(2,5-dimethyl-cyclopentadienyl-[1,2-b:4,3-b']-dithiophene)zirconium dichloride and dimethyl;

methylene(2,3,4,5-tetraisopropyl-cyclopentadienyl)-7-(2,5-dimethyl-cyclopentadienyl-[1,2-b:4,3-b']-dithiophene)zirconium dichloride and dimethyl;

isopropylidene(3-trimethylsilyl-cyclopentadienyl)-7-(2,5-dimethyl-cyclopentadienyl-[1,2-b:4,3-b']-dithiophene)zirconium dichloride and dimethyl;

isopropylidene(3-methyl-cyclopentadienyl)-7-(2,5-dimethyl-cyclopentadienyl-[1,2-b:4,3-b']-dithiophene)zirconium dichloride and dimethyl;

isopropylidene(3-methyl-cyclopentadienyl)-7-(2,5-ditrimethylsilyl-cyclopentadienyl-[1,2-b:4,3-b']-dithiophene)zirconium dichloride and dimethyl;

isopropylidene(3-ethyl-cyclopentadienyl)-7-(2,5-dimethyl-cyclopentadienyl-[1,2-b:4,3-b']-dithiophene)zirconium dichloride and dimethyl;

isopropylidene(3-isopropyl-cyclopentadienyl)-7-(2,5-dimethyl-cyclopentadienyl-[1,2-b:4,3-b']-dithiophene)zirconium dichloride and dimethyl;

isopropylidene (3-isopropyl-cyclopentadienyl)-7-(2,5-ditrimethylsilyl-cyclopentadienyl-[1,2-b:4,3-b']-dithiophene)zirconium dichloride and dimethyl;

isopropylidene(3-tert-butyl-cyclopentadienyl)-7-(2,5-dimethyl-cyclopentadienyl-[1,2-b:4,3-b']-dithiophene)zirconium dichloride and dimethyl;

isopropylidene(3-phenyl-cyclopentadienyl)-7-(2,5-dimethyl-cyclopentadienyl-[1,2-b:4,3-b']-dithiophene)zirconium dichloride and dimethyl;

isopropylidene(2,3-dimethyl-cyclopentadienyl)-7-(2,5-dimethyl-cyclopentadienyl-[1,2-b:4,3-b']-dithiophene)zirconium dichloride and dimethyl;

isopropylidene(2,3-dimethyl-cyclopentadienyl)-7-(2,5-dimethyl-cyclopentadienyl-[1,2-b:4,3-b']-dithiophene)zirconium dichloride and dimethyl;

isopropylidene(2,3-diisopropyl-cyclopentadienyl)-7-(2,5-dimethyl-cyclopentadienyl-[1,2-b:4,3-b']-dithiophene)zirconium dichloride and dimethyl;

isopropylidene(2,3-ditert-butyl-cyclopentadienyl)-7-(2,5-dimethyl-cyclopentadienyl-[1,2-b:4,3-b']-dithiophene)zirconium dichloride and dimethyl;

isopropylidene(2,3,5-trimethyl-cyclopentadienyl)-7-(2,5-dimethyl-cyclopentadienyl-[1,2-b:4,3-b']-dithiophene)zirconium dichloride and dimethyl;

isopropylidene(2,3,5-triethyl-cyclopentadienyl)-7-(2,5-dimethyl-cyclopentadienyl-[1,2-b:4,3-b']-dithiophene)zirconium dichloride and dimethyl;

isopropylidene(2,3,5-triisopropyl-cyclopentadienyl)-7-(2,5-dimethyl-cyclopentadienyl-[1,2-b:4,3-b']-dithiophene)zirconium dichloride and dimethyl;

isopropylidene(2,3,5-tritert-butyl-cyclopentadienyl)-7-(2,5-dimethyl-cyclopentadienyl-[1,2-b:4,3-b']-dithiophene)zirconium dichloride and dimethyl;

isopropylidene(2,3,4,5-tetramethyl-cyclopentadienyl)-7-(2,5-dimethyl-cyclopentadienyl-[1,2-b:4,3-b']-dithiophene)zirconium dichloride and dimethyl;

isopropylidene(2,3,4,5-tetraethyl-cyclopentadienyl)-7-(2,5-dimethyl-cyclopentadienyl-[1,2-b:4,3-b']-dithiophene)zirconium dichloride and dimethyl;

isopropylidene(2,3,4,5-tetraisopropyl-cyclopentadienyl)-7-(2,5-dimethyl-cyclopentadienyl-[1,2-b:4,3-b']-dithiophene)zirconium dichloride and dimethyl;

benzylidene(3-methyl-cyclopentadienyl)-7-(2,5-dimethyl-cyclopentadienyl-[1,2-b:4,3-b']-dithiophene)zirconium dichloride and dimethyl;

benzylidene(3-trimethylsilyl-cyclopentadienyl)-7-(2,5-ditrimethylsilyl-cyclopentadienyl-[1,2-b:4,3-b']-dithiophene)zirconium dichloride and dimethyl;

benzylidene(3-methyl-cyclopentadienyl)-7-(2,5-ditrimethylsilyl-cyclopentadienyl-[1,2-b:4,3-b']-dithiophene)zirconium dichloride and dimethyl;

benzylidene(3-methyl-cyclopentadienyl)-7-(2,5-diethyl-cyclopentadienyl-[1,2-b:4,3-b']-dithiophene)zirconium dichloride and dimethyl;

benzylidene(3-methyl-cyclopentadienyl)-7-(2,5-diethyl-cyclopentadienyl-[1,2-b:4,3-b']-dioxazole)zirconium dichloride and dimethyl;

methylene(3-trimethylsilyl-cyclopentadienyl)-4-(cyclopentadienyl-[2,1-b:3,4-b']-dithiophene)zirconium dichloride and dimethyl;

methylene(cyclopentadienyl)-4-(2,5-ditrimethylsilyl-cyclopentadienyl-[2,1-b:3,4-b']-dithiophene)zirconium dichloride and dimethyl;

methylene(cyclopentadienyl)-4-(2,5ditrimethylsilyl-cyclopentadienyl-[2,1-b:3,4-b']-dioxazole)zirconium dichloride and dimethyl;

methylene(3-trimethylsilyl-cyclopentadienyl)-4-(2,6-ditrimethylsilyl-cyclopentadienyl-[2,1-b:3,4-b']-dithiophene)zirconium dichloride and dimethyl;

methylene(cyclopentadienyl)-4-(2,6-dimethylphosphinocyclopentadienyl-[2,1-b:3,4-b']dithiophene)zirconium dichloride and dimethyl;

methylene(cyclopentadienyl)-4-(2,6-dimethylphosphinocyclopentadienyl-[2,1-b:3,4-b']dioxazole)zirconium dichloride and dimethyl;

methylene(cyclopentadienyl)-4-(2,6-diphenylylphosphinocyclopentadienyl-[2,1-b:3,4-b']dithiophene)zirconium dichloride and dimethyl;

methylene(cyclopentadienyl)-4-(2,6-dimethoxyphosphinocyclopentadienyl-[2,1-b:3,4-b']dithiophene)zirconium dichloride and dimethyl;

methylene(cyclopentadienyl)-4-(2,6-dimethoxyborylcyclopentadienyl-[2,1-b:3,4-b']dithiophene)zirconium dichloride and dimethyl;

methylene(cyclopentadienyl)-4-(2,6-dimethoxycyclopentadienyl-[2,1-b:3,4-b']dithiophene)zirconium dichloride and dimethyl;

methylene(3-methoxycyclopentadienyl)-4-(2,6-dimethoxycyclopentadienyl-[2,1-b:3,4-b']dithiophene)zirconium dichloride and dimethyl;

methylene(cyclopentadienyl)-4-(2,6-dithioclopentadienyl-[2,1-b:3,4-b']dithiophene)zirconium dichloride and dimethyl;

methylene(3-methyl-cyclopentadienyl)-4-(cyclopentadienyl-[2,1-b:3,4-b']-dithiophene)zirconium dichloride and dimethyl;

methylene(3-ethyl-cyclopentadienyl)-4-(cyclopentadienyl-[2,1-b:3,4-b']-dithiophene)zirconium dichloride and dimethyl;

methylene(3-isopropyl-cyclopentadienyl)-4-(cyclopentadienyl-[2,1-b:3,4-b']-dithiophene)zirconium dichloride and dimethyl;

methylene(3-tert-butyl-cyclopentadienyl)-4-(cyclopentadienyl-[2,1-b:3,4-b']-dithiophene)zirconium dichloride and dimethyl;

methylene(3-phenyl-cyclopentadienyl)-4-(cyclopentadienyl-[2,1-b:3,4-b']-dithiophene)zirconium dichloride and dimethyl;

methylene(2,3-dimethyl-cyclopentadienyl)-4-(cyclopentadienyl-[2,1-b:3,4-b']-dithiophene)zirconium dichloride and dimethyl;

methylene(2,3-diethyl-cyclopentadienyl)-4-(cyclopentadienyl-[2,1-b:3,4-b']-dithiophene)zirconium dichloride and dimethyl;

methylene(2,3-diisopropyl-cyclopentadienyl)-4-(cyclopentadienyl-[2,1-b:3,4-b']-dithiophene)zirconium dichloride and dimethyl;

methylene(2,3-ditert-butyl-cyclopentadienyl)-4-(cyclopentadienyl-[2,1-b:3,4-b']-dithiophene)zirconium dichloride and dimethyl;

methylene(2,3,5-trimethyl-cyclopentadienyl)-4-(cyclopentadienyl-[2,1-b:3,4-b]-dithiophene)zirconium dichloride and dimethyl;

methylene(2,3,5-triethyl-cyclopentadienyl)-4-(cyclopentadienyl-[2,1-b:3,4-b']-dithiophene)zirconium dichloride and dimethyl;

methylene(2,3,5-triisopropyl-cyclopentadienyl)-4-(cyclopentadienyl-[2,1-b:3,4-b']-dithiophene)zirconium dichloride and dimethyl;

methylene(2,3,5-tritert-butyl-cyclopentadienyl)-4-(cyclopentadienyl-[2,1-b:3,4-b']-dithiophene)zirconium dichloride and dimethyl;

methylene(2,3,4,5-tetramethyl-cyclopentadienyl)-4-(cyclopentadienyl-[2,1-b:3,4-b']-dithiophene)zirconium dichloride and dimethyl;

methylene(2,3,4,5-tetraethyl-cyclopentadienyl)-4-(cyclopentadienyl-[2,1-b:3,4-b']-dithiophene)zirconium dichloride and dimethyl;
methylene(2,3,4,5-tetraisopropyl-cyclopentadienyl)-4-(cyclopentadienyl-[2,1-b:3,4-b']-dithiophene)zirconium dichloride and dimethyl;
isopropylidene(3-trimethylsilyl-cyclopentadienyl)-4-(cyclopentadienyl-[2,1-b:3,4-b']-dithiophene)zirconium dichloride and dimethyl;
isopropylidene(cyclopentadienyl)-4-(2,6-ditrimethylsilyl-cyclopentadienyl-[2,1-b:3,4-b']-dithiophene)zirconium dichloride and dimethyl;
isopropylidene(3-trimethylsilyl-cyclopentadienyl)-4-(2,6-ditrimethylsilyl-cyclopentadienyl-[2,1-b:3,4-b']-dithiophene)zirconium dichloride and dimethyl;
isopropylidene(cyclopentadienyl)-4-(2,6-dimethylphosphinocyclopentadienyl-[2,1-b:3,4-b']dithiophene)zirconium dichloride and dimethyl;
isopropylidene(cyclopentadienyl)-4-(2,6-diphenylylphosphinocyclopentadienyl-[2,1-b:3,4-b']dithiophene)zirconium dichloride and dimethyl;
isopropylidene(cyclopentadienyl)-4-(2,6-dimethoxyphosphinocyclopentadienyl-[2,1-b:3,4-b']dithiophene)zirconium dichloride and dimethyl;
isopropylidene(cyclopentadienyl)-4-(2,6-dimethoxyborylcyclopentadienyl-[2,1-b:3,4-b']dithiophene)zirconium dichloride and dimethyl;
isopropylidene(cyclopentadienyl)-4-(2,6-dimethoxycyclopentadienyl-[2,1-b:3,4-b']dithiophene)zirconium dichloride and dimethyl;
isopropylidene(cyclopentadienyl)-4-(2,6-dithioclopentadienyl-[2,1-b:3,4-b']dithiophene)zirconium dichloride and dimethyl;
isopropylidene(3-methyl-cyclopentadienyl)-4-(cyclopentadienyl-[2,1-b:3,4-b']-dithiophene)zirconium dichloride and dimethyl;
isopropylidene(3-methyl-cyclopentadienyl)-4-(cyclopentadienyl-[2,1-b:3,4-b']-dioxazole)zirconium dichloride and dimethyl;
isopropylidene(3-ethyl-cyclopentadienyl)-4-(cyclopentadienyl-[2,1-b:3,4-b']-dithiophene)zirconium dichloride and dimethyl;
isopropylidene(3-isopropyl-cyclopentadienyl)-4-(cyclopentadienyl-[2,1-b:3,4-b']-dithiophene)zirconium dichloride and dimethyl;
isopropylidene(3-tert-butyl-cyclopentadienyl)-4-(cyclopentadienyl-[2,1-b:3,4-b']-dithiophene)zirconium dichloride and dimethyl;
isopropylidene(3-phenyl-cyclopentadienyl)-4-(cyclopentadienyl-[2,1-b:3,4-b']-dithiophene)zirconium dichloride and dimethyl;
isopropylidene(2,3-dimethyl-cyclopentadienyl)-4-(cyclopentadienyl-[2,1-b:3,4-b']-dithiophene)zirconium dichloride and dimethyl;
isopropylidene(2,3-diethyl-cyclopentadienyl)-4-(cyclopentadienyl-[2,1-b:3,4-b']-dithiophene)zirconium dichloride and dimethyl;
isopropylidene(2,3-diisopropyl-cyclopentadienyl)-4-(cyclopentadienyl-[2,1-b:3,4-b']-dithiophene)zirconium dichloride and dimethyl;
isopropylidene(2,3-ditert-butyl-cyclopentadienyl)-4-(cyclopentadienyl-[2,1-b:3,4-b']-dithiophene)zirconium dichloride and dimethyl;
isopropylidene(2,3,5-trimethyl-cyclopentadienyl)-4-(cyclopentadienyl-[2,1-b:3,4-b']-dithiophene)zirconium dichloride and dimethyl;
isopropylidene(2,3,5-triethyl-cyclopentadienyl)-4-(cyclopentadienyl-[2,1-b:3,4-b']-dithiophene)zirconium dichloride and dimethyl;
isopropylidene(2,3,5-triisopropyl-cyclopentadienyl)-4-(cyclopentadienyl-[2,1-b:3,4-b']-dithiophene)zirconium dichloride and dimethyl;
isopropyldene(2,3,5-tritert-butyl-cyclopentadienyl)-4-(cyclopentadienyl-[2,1-b:3,4-b']-dithiophene)zirconium dichloride and dimethyl;
isopropylidene(2,3,4,5-tetramethyl-cyclopentadienyl)-4-(cyclopentadienyl-[2,1-b:3,4-b']-dithiophene)zirconium dichloride and dimethyl;
isopropylidene(2,3,4,5-tetraethyl-cyclopentadienyl)-4-(cyclopentadienyl-[2,1-b:3,4-b']-dithiophene)zirconium dichloride and dimethyl;
isopropylidene(2,3,4,5-tetraisopropyl-cyclopentadienyl)-4-(cyclopentadienyl-[2,1-b:3,4-b']-dithiophene)zirconium dichloride and dimethyl;
methylene(3-trimethylsilyl-cyclopentadienyl)-4-(2,6-dimethyl-cyclopentadienyl-[2,1-b:3,4-b']-dithiophene)zirconium dichloride and dimethyl;
methylene(3-methyl-cyclopentadienyl)-4-(2,6-dimethyl-cyclopentadienyl-[2,1-b:3,4-b']-dithiophene)zirconium dichloride and dimethyl;
methylene(3-methyl-cyclopentadienyl)-4-(2,6-ditrimethylsilyl-cyclopentadienyl-[2,1-b:3,4-b']-dithiophene)zirconium dichloride and dimethyl;
methylene(3-ethyl-cyclopentadienyl)-4-(2,6-dimethyl-cyclopentadienyl-[2,1-b:3,4-b']-dithiophene)zirconium dichloride and dimethyl;
methylene(3-isopropyl-cyclopentadienyl)-4-(2,6-dimethyl-cyclopentadienyl-[2,1-b:3,4-b']-dithiophene)zirconium dichloride and dimethyl;
methylene(3-isopropyl-cyclopentadienyl)-4-(2,6-ditrimethylsilyl-cyclopentadienyl-[2,1-b:3,4-b']-dithiophene)zirconium dichloride and dimethyl;
methylene(3-tert-butyl-cyclopentadienyl)-4-(2,6-dimethyl-cyclopentadienyl-[2,1-b:3,4-b']-dithiophene)zirconium dichloride and dimethyl;
methylene(3-phenyl-cyclopentadienyl)-4-(2,6-dimethyl-cyclopentadienyl-[2,1-b:3,4-b']-dithiophene)zirconium dichloride and dimethyl;
methylene(2,3-dimethyl-cyclopentadienyl)-4-(2,6-dimethyl-cyclopentadienyl-[2,1-b:3,4-b']-dithiophene)zirconium dichloride and dimethyl;
methylene(2,3-diethyl-cyclopentadienyl)-4-(2,6-dimethyl-cyclopentadienyl-[2,1-b:3,4-b']-dithiophene)zirconium dichloride and dimethyl;
methylene(2,3-diisopropyl-cyclopentadienyl)-4-(2,6-dimethyl-cyclopentadienyl-[2,1-b:3,4-b']-dithiophene)zirconium dichloride and dimethyl;
methylene(2,3-ditert-butyl-cyclopentadienyl)-4-(2,6-dimethyl-cyclopentadienyl-[2,1-b:3,4-b']-dithiophene)zirconium dichloride and dimethyl;
methylene(2,3,5-trimethyl-cyclopentadienyl)-4-(2,6-dimethyl-cyclopentadienyl-[2,1-b:3,4-b']-dithiophene)zirconium dichloride and dimethyl;
methylene(2,3,5-triethyl-cyclopentadienyl)-4-(2,6-dimethyl-cyclopentadienyl-[2,1-b:3,4-b']-dithiophene)zirconium dichloride and dimethyl;
methylene(2,3,5-triisopropyl-cyclopentadienyl)-4-(2,6-dimethyl-cyclopentadienyl-[2,1-b:3,4-b']-dithiophene)zirconium dichloride and dimethyl;
methylene(2,3,5-tritert-butyl-cyclopentadienyl)-4-(2,6-dimethyl-cyclopentadienyl-[2,1-b:3,4-b']-dithiophene)zirconium dichloride and dimethyl;
methylene(2,3,4,5-tetramethyl-cyclopentadienyl)-4-(2,6-dimethyl-cyclopentadienyl-[2,1-b:3,4-b']-dithiophene)zirconium dichloride and dimethyl;
methylene(2,3,4,5-tetraethyl-cyclopentadienyl)-4-(2,6-dimethyl-cyclopentadienyl-[2,1-b:3,4-b']-dithiophene)zirconium dichloride and dimethyl;

methylene(2,3,4,5-tetraisopropyl-cyclopentadienyl)-4-(2,6-dimethyl-cyclopentadienyl-[2,1-b:3,4-b']-dithiophene) zirconium dichloride and dimethyl;
isopropylidene(3-trimethylsilyl-cyclopentadienyl)-4-(2,6-dimethyl-cyclopentadienyl-[2,1-b:3,4-b']-dithiophene) zirconium dichloride and dimethyl;
isopropylidene(3-methyl-cyclopentadienyl)-4-(2,6-dimethyl-cyclopentadienyl-[2,1-b:3,4-b']-dithiophene) zirconium dichloride and dimethyl;
isopropylidene(3-methyl-cyclopentadienyl)-4-(2,6-ditrimethylsilyl-cyclopentadienyl-[2,1-b:3,4-b']-dithiophene)zirconium dichloride and dimethyl;
isopropylidene(3-ethyl-cyclopentadienyl)-4-(2,6-dimethyl-cyclopentadienyl-[2,1-b:3,4-b']-dithiophene)zirconium dichloride and dimethyl;
isopropylidene(3-isopropyl-cyclopentadienyl)-1-(2,6-dimethyl-cyclopentadienyl-[2,1-b:3,4-b']-dithiophene) zirconium dichloride and dimethyl;
isopropylidene(3-isopropyl-cyclopentadienyl)-4-(2,6-ditrimethylsilyl-cyclopentadienyl-[2,1-b:3,4-b']-dithiophene)zirconium dichloride and dimethyl;
isopropylidene(3-tert-butyl-cyclopentadienyl)-4-(2,6-dimethyl-cyclopentadienyl-[2,1-b:3,4-b']-dithiophene) zirconium dichloride and dimethyl;
isopropylidene(3-phenyl-cyclopentadienyl)-4-(2,6-dimethyl-cyclopentadienyl-[2,1-b:3,4-b']-dithiophene) zirconium dichloride and dimethyl;
isopropylidene(2,3-dimethyl-cyclopentadienyl)-4-(2,6-dimethyl-cyclopentadienyl-[2,1-b:3,4-b']-dithiophene) zirconium dichloride and dimethyl;
isopropylidene(2,3-dimethyl-cyclopentadienyl)-4-(2,6-dimethyl-cyclopentadienyl-[2,1-b:3,4-b']-dioxazole) zirconium dichloride and dimethyl;
isopropylidene(2,3-dimethyl-cyclopentadienyl)-4-(2,6-dimethyl-cyclopentadienyl-[2,1-b:3,4-b']-dithiophene) zirconium dichloride and dimethyl;
isopropylidene(2,3-diisopropyl-cyclopentadienyl)-4-(2,6-dimethyl-cyclopentadienyl-[2,1-b:3,4-b']-dithiophene) zirconium dichloride and dimethyl;
isopropylidene(2,3-ditert-butyl-cyclopentadienyl)-4-(2,6-dimethyl-cyclopentadienyl-[2,1-b:3,4-b']-dithiophene) zirconium dichloride and dimethyl;
isopropylidene(2,3,5-trimethyl-cyclopentadienyl)-4-(2,6-dimethyl-cyclopentadienyl-[2,1-b:3,4-b']-dithiophene) zirconium dichloride and dimethyl;
isopropylidene(2,3,5-triethyl-cyclopentadienyl)-4-(2,6-dimethyl-cyclopentadienyl-[2,1-b:3,4-b']-dithiophene) zirconium dichloride and dimethyl;
isopropylidene(2,3,5-triisopropyl-cyclopentadienyl)-4-(2,6dimethyl-cyclopentadienyl-[2,1-b:3,4-b']-dithiophene) zirconium dichloride and dimethyl;
isopropylidene(2,3,5-tritert-butyl-cyclopentadienyl)-4-(2,6-dimethyl-cyclopentadienyl-[2,1-b:3,4-b']-dithiophene) zirconium dichloride and dimethyl;
isopropylidene(2,3,4,5-tetramethyl-cyclopentadienyl)-4-(2,6-dimethyl-cyclopentadienyl-[2,1-b:3,4-b']-dithiophene) zirconium dichloride and dimethyl;
isopropylidene(2,3,4,5-tetraethyl-cyclopentadienyl)-4-(2,6-dimethyl-cyclopentadienyl-[2,1-b:3,4-b']-dithiophene) zirconium dichloride and dimethyl;
isopropylidene(2,3,4,5-tetraisopropyl-cyclopentadienyl)-4-(2,6-dimethyl-cyclopentadienyl-[2,1-b:3,4-b']-dithiophene)zirconium dichloride and dimethyl;
benzylidene(3-trimethylsilyl-cyclopentadienyl)-4-(2,6-dimethyl-cyclopentadienyl-[2,1-b:3,4-b']-dithiophene) zirconium dichloride and dimethyl;
benzylidene(3-methyl-cyclopentadienyl)-4-(2,6-dimethyl-cyclopentadienyl-[2,1-b:3,4-b']-dithiophene)zirconium dichloride and dimethyl;
benzylidene(3-methyl-cyclopentadienyl)-4-(cyclopentadienyl-[2,1-b:3,4-b']-dithiophene)zirconium dichloride and dimethyl;
isopropylidene(3-trimethylsilyl-cyclopentadienyl)-4-(2-methyl-6-ethyl-cyclopentadienyl-[2,1-b:3,4-b']-dithiophene)zirconium dichloride and dimethyl;
isopropylidene(3-methyl-cyclopentadienyl)-4-(2-methyl-6-ethyl-cyclopentadienyl-[2,1-b:3,4-b']-dithiophene) zirconium dichloride and dimethyl;
methylene(3-trimethylsilyl-cyclopentadienyl)-4-(2-methyl-6-ethyl-cyclopentadienyl-[2,1-b:3,4-b']-dithiophene) zirconium dichloride and dimethyl;
methylene(3-methyl-cyclopentadienyl)-4-(2-methyl-6-ethyl-cyclopentadienyl-[2,1-b:3,4-b']-dithiophene) zirconium dichloride and dimethyl;
isopropylidene(3-trimethylsilyl-cyclopentadienyl)-4-(2-methyl-6-isopropyl-cyclopentadienyl-[2,1-b:3,4-b']-dithiophene)zirconium dichloride and dimethyl;
isopropylidene(3-methyl-cyclopentadienyl)-4-(2-methyl-6-isopropyl-cyclopentadienyl-[2,1-b:3,4-b']-dithiophene) zirconium dichloride and dimethyl.

Metallocene compounds of formula (I) can be prepared starting from a ligand of formula (II):

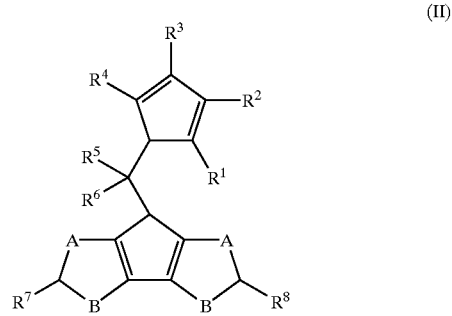

and/or its double bond isomers, wherein the rings containing A and B have double bonds in any of the allowed position, having an aromatic character and A, B, $R^1$, $R^2$, $R^3$, $R^4$, $R^5$, $R^6$, $R^7$ and $R^8$ are defined as above.

Thus a further object of the present invention is a compound of formula (II)
isopropylidene(cyclopentadiene)-7-(cyclopentadithiophene),
isopropylidene(3-methyl-cyclopentadiene)-7-(cyclopentadithiophene);
isopropylidene(3-ethyl-cyclopentadiene)-7-(cyclopentadithiophene);
isopropylidene(3-t-butyl-cyclopentadiene)-7-(cyclopentadithiophene);
isopropylidene(3-n-butyl-cyclopentadiene)-7-(cyclopentadithiophene);
isopropylidene(3-trimethylsilyl-cyclopentadiene)-7-(cyclopentadithiophene) and
isopropylidene (3-i-propylcyclopentadiene)-7-(cyclopentadithiophene) being excluded.

The ligand of formula (II) can be prepared according to a process comprising the following steps:
i) treating the compound of formula (III) with at least one equivalent of a base;

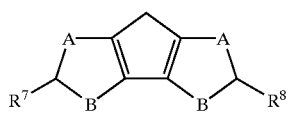
(III)

wherein the rings containing A and B have a double bond in the allowed position having an aromatic character, A, B, $R^7$ and $R^8$ are defined as above;

ii) contacting the thus obtained corresponding anionic compound of formula (III) with a compound of formula (IV):

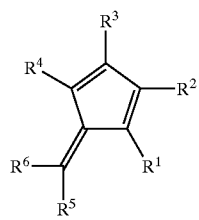
(IV)

wherein $R^1$, $R^2$, $R^3$, $R^4$, $R^5$ and $R^6$ are defined as above described, and iii) treating the obtained product with a protonating agent.

The base used in step i) is preferably selected from hydroxides and hydrides of alkali- and earth-alkali metals, metallic sodium and potassium and organometallic lithium salts. Most preferably, said base is methyllithium or n-butyllithium.

Preferably the protonating agent used in the above process is a quaternary ammonium salt and most preferably the protonating agent is ammonium chloride.

When both $R^7$ and $R^8$ are hydrogen the correspondent compound of formula (III) is obtained according to WO 98/22486.

In the case which B is a $CR^9$ group and preferably $R^7$ and $R^8$ which may be the same as or different from each other, are selected from a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_2$-arylalkyl radical, optionally containing heteroatoms belonging to groups 13 or 15–17 of the Periodic Table of the Elements, the corresponding compound of formula (III) can be obtained with a process comprising the following steps:

i) treating a compound of formula (V):

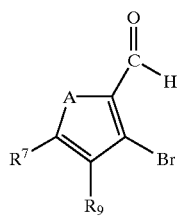
(V)

wherein A is sulfur or oxygen, with a compound of formula (VI):

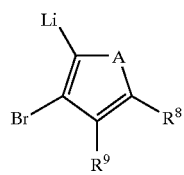
(VI)

wherein A is sulfur or oxygen, ii) contacting the thus obtained product with a reducing agent in a molar ratio between said reducing agent and the product obtained under i) of at least 1;

iii) contacting the product obtained under ii) with a compound selected from an organolithium compound, sodium and potassium in a molar ratio between said compound and the product obtained in step ii) of equal to or greater than 2;

iv) treating the thus obtained product with an agent selected from the group consisting of copper chloride, iodine and Mg/Pd., in order to obtain a compound of general formula (VII):

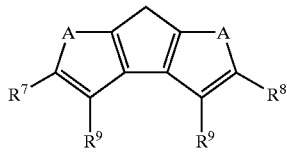
(VII)

When B is sulfur or oxygen and A is a $CR^9$ group and preferably $R^7$ and $R^8$ which may be the same as or different from each other, are selected from a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms belonging to groups 13 or 15–17 of the Periodic Table of the Elements, the correspondent compound of formula (III) can be obtained according to the process comprising the following steps:

i) contacting a compound of formula (VIII):

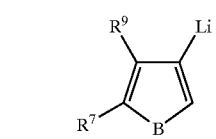
(VIII)

wherein B is sulfur or oxygen,
with a compound of formula (IX):

(IX)

wherein B is sulfur or oxygen,
and subsequently treating with a neutralization agent;

ii) treating the thus obtained product with a reducing agent in a molar ratio between said reducing agent and the compound obtained under i) of at least 1;

iii) contacting the thus obtained product with a mixture of an organolithium compound and tetramethylethylenediamine (TMEDA) in a molar ratio between said mixture and the product obtained under ii) of at least 2,
iv) contacting the thus obtained product with an agent selected from the group consisting of copper chloride, iodine and Mg/Pd., in order to obtain a compound of formula (X):

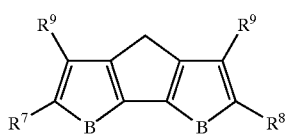

(X)

An alternative process for preparing the compound of formula (III) when A is S or O and preferably $R^7$ and $R^8$ which may be the same as or different from each other, are selected from a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms belonging to groups 13 or 15–17 of the Periodic Table of the Elements, comprises the following steps:

i) contacting an equimolar mixture of compounds of formulae (XI) and (XII):

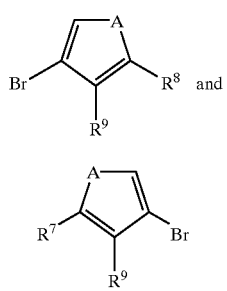

XI

XII wherein A are sulfur or oxygen,
with a Lewis acid or a mixture of a Lewis acid and a protonic acid;
ii) treating the thus obtained product with $CH_2O$ in a molar ratio between said mixture and $CH_2O$ of a range between 10:1 and 1:10;
iii) contacting the thus obtained product with a compound selected from an organolithium compound, sodium and potassium;
iv) contacting the thus obtained product with an agent selected from the group consisting of copper chloride, iodine and Mg/Pd., in order to obtain a compound of general formula (VII)

The Lewis acid used in the above process is preferably selected from zinc dichloride, cadmium dichloride, mercury dichloride, tin tetrachloride, trifluoroborane, zirconium tetrachloride, titanium tetrachloride. Most preferably, the Lewis acid is zinc dichloride.

Another alternative process for preparing the compound of formula (III) when A is S or O and preferably $R^7$ and $R^8$ which may be the same as or different from each other, are selected from a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms belonging to groups 13 or 15–17 of the Periodic Table of the Elements, comprises the following steps:

i) contacting a compound of formula (XIII):

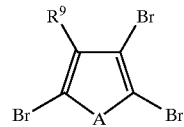

(XIII)

with a base selected from an organolithium compound, sodium or potassium; treating with a formic ester, wherein the molar ratio between said ester and the compound of formula (XIII) is at least 1:2, and subsequently treating the obtained product with a reducing agent in order to obtain a compound of formula (XIV):

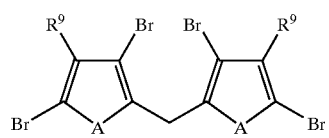

(XIV)

ii) contacting the compound of formula (XIV) with a base selected from an organolithium compound, sodium or potassium and subsequently treating the dimetallated compound with an alkylating agent to obtain the compound of formula (XV);

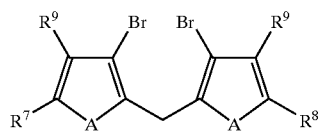

(XV)

or alternatively treating the dimetallated compound with an ester of boric acid and a protonating agent in order to obtain the compound of formula (XVI):

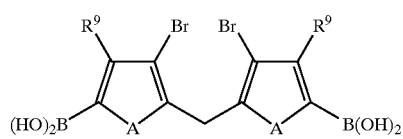

(XVI)

and subsequently contacting with a mixture of an alkylating agent in the presence of an transition metal complex compound for obtaining the compound of formula (XV);
iii) contacting the alkylated compound obtained by step b) with a coupling agent; agent selected from the group consisting of copper chloride, iodine and Mg/Pd in order to obtain the compound of formula (VII).

Preferably the alkylating agent is selected from dimethylsulphate ($Me_2SO_4$), trimethylchlorosilane ($Me_3SiCl$) and a mixture of compounds of formulae $R^3Y'$ and $R^4Y'$, wherein $R^3$ and $R^4$ are defined as above and $Y'$ is selected from chloride, bromide and iodide. Preferably $Y'$ is a chlorine. Preferably the transition metal complex compound is $PdCl_2$ (dppf).

In the above processes the agent used is preferably copper chloride; the reducing agent is preferably a mixture of $AlCl_3/LiAlH_4$; the organolithium compound used above is preferably butyllithium.

The compound of formula (III) is an important intermediate for preparing the ligand of formula (II) and consequently the metallocene compound of formula (I). Thus a further object of the present invention is a compound of formula (III)

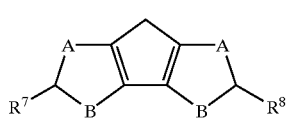
(III)

wherein the rings containing A and B have a double bond in the allowed position having an aromatic character; A and B are as above described and $R^7$, and $R^8$ which may be the same as or different from each other, are selected from a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms belonging to groups 13 or 15–17 of the Periodic Table of the Elements.

Preferably B is a CH group, A is sulfur and $R^7$ and $R^8$ which may be the same as or different from each other, are selected from a $C_1$–$C_{20}$-alkyl, $C_3$–$C_{20}$-aryl.

Ligands of formula (II) can suitably be used as intermediates for the preparation of metallocenes of formula (I).

A further aspect of the present invention is a process for the preparation of a metallocene compound of the formula (I) comprising the following steps:
a) contacting a compound of formula (II) as defined above with a base, wherein the molar ratio between said base and the compound of formula (II) is at least 2;
b) contacting with a compound of formula $MX_{p+2}$, M and X being defined as mentioned above and p is an integer being equal to the oxidation state of the metal M minus 2.

Preferably, the base is butyllithium.

Preferably $MX_{p+2}$ is selected from $ZrCl_4$, $TiCl_4$, $HfCl_4$ and the $C_1$–$C_6$-alkyl analogues thereof. The reaction is carried out in an inert solvent such as toluene, tetrahydrofurane, benzene, diethyl ether, hexane and the like at a temperature range from $-78°$ C. to $100°$ C.

In the case in which at least one substituent X in the metallocene compound of the formula (I) is different from halogen an alternative process for preparing it, consists in preparing the dihalogen derivative i.e. the complex wherein both X are halogen and then substituting the halogen atom with the appropriate X group generally applied methods. For example, if the desired substituents X are alkyl groups, the metallocenes can be made to react with alkylmagnesium halides (Grignard reagents) or with alkyllithium compounds. General methods for substitution X by substituents other than halogen such as sulfur, phosphorus, oxygen, etc. are described in Chem. Rev. 1994, 94, 1661–1717, and the therein cited references.

The alumoxane used as component (B), in the polymerization process as above described, can be obtained by reacting water with an organo-aluminium compound of formula $H_jAlR^{12}_{3-j}$ or $H_jAl_2R^{12}_{6-j}$, where $R^{12}$ substituents, same or different, are hydrogen atoms, $C_1$–$C_{20}$-alkyl, $C_3$–$C_{20}$-cyclalkyl, $C_6$–$C_{20}$-aryl, $C_7$–$C_{20}$-alkylaryl or $C_7$–$C_{20}$-arylalkyl, optionally containing silicon or germanium atoms with the proviso that at least one $R^{12}$ is different from halogen, and J ranges from 0 to 1, being also a non-integer number. In this reaction the molar ratio of Al/water is preferably comprised between 1:1 and 100:1.

The molar ratio between aluminium and the metal of the metallocene is comprised between about 10:1 and about 20000:1, and more preferably between about 100:1 and about 5000:1.

The alumoxanes used in the catalyst according to the invention are considered to be linear, branched or cyclic compounds containing at least one group of the type:

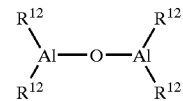

wherein the $R^{12}$ substituents, same or different, are above described.

In particular, alumoxanes of the formula:

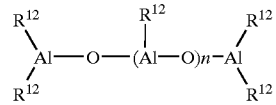

can be used in the case of linear compounds, wherein n is 0 or an integer from 1 to 40 and the $R^{12}$ substituents are defined as above, or alumoxanes of the formula:

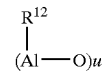

can be used in the case of cyclic compounds, wherein u is an integer from 2 to 40 and the $R^{12}$ substituents are defined as above.

Examples of alumoxanes suitable for use according to the present invention are methylalumoxane (MAO), tetra-(isobutyl)alumoxane (TIBAO), tetra-(2,4,4-trimethyl-pentyl)alumoxane (TIOAO), tetra-(2,3-dimethylbutyl) alumoxane (TDMBAO) and tetra-(2,3,3-trimethylbutyl) alumoxane (TTMBAO).

Particularly interesting cocatalysts are those described in WO 99/21899 and in PCT/EP00/09111 in which the alkyl and aryl groups have specific branched patterns.

Non-limiting examples of aluminium compounds according to said PCT applications are:
tris(2,3,3-trimethyl-butyl)aluminium, tris(2,3-dimethyl-hexyl)aluminium, tris(2,3-dimethyl-butyl)aluminium, tris(2,3-dimethyl-pentyl)aluminium, tris(2,3-dimethyl-heptyl)aluminium, tris(2-methyl-3-ethyl-pentyl) aluminium, tris(2-methyl-3-ethyl-hexyl)aluminium, tris(2-methyl-3-ethyl-heptyl)aluminium, tris(2-methyl-3-propyl-hexyl)aluminium, tris(2-ethyl-3-methyl-butyl) aluminium, tris(2-ethyl-3-methyl-pentyl)aluminium, tris(2,3-diethyl-pentyl)aluminium, tris(2-propyl-3-methyl-butyl)aluminium, tris(2-isopropyl-3-methyl-butyl) aluminium, tris(2-isobutyl-3-methyl-pentyl)aluminium, tris(2,3,3-trimethyl-pentyl)aluminium, tris(2,3,3-trimethyl-hexyl)aluminium, tris(2-ethyl-3,3-dimethyl-butyl)aluminium, tris(2-ethyl-3,3-dimethyl-pentyl) aluminium, tris(2-isopropyl-3,3-dimethyl-butyl) aluminium, tris(2-trimethylsilyl-propyl)aluminium, tris (2-methyl-3-phenyl-butyl)aluminium, tris(2-ethyl-3-phenyl-butyl)aluminium, tris(2,3-dimethyl-3-phenyl-butyl)aluminium, tris(2-phenyl-propyl)aluminium, tris[2-(4-fluoro-phenyl)-propyl]aluminium, tris[2-(4-chloro-phenyl)-propyl]aluminium, tris[2-(3-isopropyl-phenyl)-propyl]aluminium, tris(2-phenyl-butyl)aluminium, tris(3-methyl-2-phenyl-butyl)aluminium, tris(2-phenyl-pentyl) aluminium, tris[2-(pentafluorophenyl)-propyl] aluminium, tris[2,2-diphenyl-ethyl]aluminium and tris[2-phenyl-2-methyl-propyl]aluminium, as well as the corresponding compounds wherein one of the hydrocarbyl groups is replaced by an hydrogen atom, and those wherein one or two of the hydrocarbyl groups are replaced by an isobutyl group.

Amongst the above aluminium compounds, trimethylaluminium (TMA), triisobutylaluminium (TIBAL), tris(2,4,4-trimethyl-pentyl)aluminium (TIOA), tris(2,3-dimethylbutyl)aluminium (TDMBA) and tris(2,3,3-trimethylbutyl)aluminium (TTMBA) are preferred.

Non-limiting examples of compounds able to form an alkylmetallocene cation are compounds of formula $D^+E^-$, wherein $D^+$ is a Brønsted acid, able to give a proton and to react irreversibly with a substituent X of the metallocene of formula (I) and $E^-$ is a compatible anion, which is able to stabilize the active catalytic species originating from the reaction of the two compounds, and which is sufficiently labile to be able to be removed by an olefinic monomer. Preferably, the anion $Z^-$ consists of one or more boron atoms. More preferably, the anion $Z^-$ is an anion of the formula $BAr_4^{(-)}$, wherein the substituents Ar which can be identical or different are aryl radicals such as phenyl, pentafluorophenyl or bis(trifluoromethyl)phenyl. Tetrakis-pentafluorophenyl borate is particularly preferred. Moreover, compounds of the formula $BAr_3$ can conveniently be used. Compounds of this type are described, for example, in the published International patent application WO 92/00333, the content of which is incorporated in the present description.

The catalysts of the present invention can also be used on supports. This is achieved by depositing the metallocene compound (A) or the product of the reaction thereof with the component (B), or the component (B) and then the metallocene compound (A) on supports such as, for example, silica, alumina, magnesium halides, styrene/divinylbenzene copolymers, polyethylene or polypropylene.

A suitable class of supports which can be used consists of porous organic supports functionalized with groups having active hydrogen atoms. Particularly suitable are those in which the organic support is a partially crosslinked styrene polymer. Supports of this type are described in European application EP-633 272.

Another class of inert supports which is particularly suitable for use according to the invention is that of the olefin, particularly propylene, porous prepolymers described in International application WO 95/26369.

A further suitable class of inert supports which can be used according to the invention is that of the porous magnesium halides such as those described in International application WO 95/32995.

The solid compound thus obtained, in combination with the further addition of the alkylaluminium compound either as such or prereacted with water if necessary, can be usefully employed in the gas-phase polymerization.

The process for the polymerization of olefins according to the invention can be carried out in the liquid phase in the presence or absence of an inert hydrocarbon solvent, or in the gas phase. The hydrocarbon solvent can be either aromatic such as toluene, or aliphatic such as propane, hexane, heptane, isobutane or cyclohexane.

The polymerization temperature is generally between $-100°$ C. and $+200°$ C. and, particularly between $10°$ C. and $+90°$ C. The polymerization pressure is generally between 0,5 and 100 bar.

The lower the polymerization temperature, the higher are the resulting molecular weights of the polymers obtained.

The polymerization yields depend on the purity of the metallocene compound of the catalyst. The metallocene compounds obtained by the process of the invention can therefore be used as such or can be subjected to purification treatments.

The components of the catalyst can be brought into contact with each other before the polymerization. The pre-contact concentrations are generally between 1 and $10^{-8}$ mol/l for the metallocene component (A), while they are generally between 10 and $10^{-8}$ mol/l for the component (B). The pre-contact is generally effected in the presence of a hydrocarbon solvent and, if appropriate, of small quantities of monomer.

By the process according to the present invention ethylene homopolymers are obtainable having high molecular weights. The ethylene polymers of the present invention have intrinsic viscosity (I.V.) values generally higher than 0.5 dl/g, more typically higher than 1.0 dl/g. Particularly in the case of ethylene homopolymers, the intrinsic viscosity can reach values as high as 5.0 dl/g.

In the copolymers obtainable by the process of the invention, the molar content of ethylene derived units is generally higher than 40%, and preferably it is between 50% and 99%, and more preferably it is between 80% and 98%.

The molar content of alpha-olefin derived units is preferably between 0% and 60% and, more preferably, between 1% and 50%, and most preferably between 2% and 20%.

Non-limiting examples of alpha-olefins which can be used as alpha-olefins in the process of the invention are propylene, 1-butene, 1-pentene, 4methyl-1-pentene, 1-hexene, 1-octene, 4,6-dimethyl-1-heptene, 1-decene, 1-dodecene, 1-tetradecene, 1-hexadecene, 1-octadecene, 1-eicosene and allylcyclohexane.

Non-limiting examples of cycloolefins that can be used as comonomers in the process of the invention are cyclopentene, cyclohexene and norbornene.

The copolymers according to the invention can also contain units derived from polyenes. The content of polyene derived units, if any, is preferably between 0% and 30% by mol and, more preferably between 0% and 20%.

The polyenes that can be used as comonomers in the copolymers according to the present invention are included in the following classes:

non-conjugated diolefins able to cyclopolymerize such as, for example, 1,5-hexadiene, 1-6-heptadiene and 2-methyl-1,5-hexadiene;

dienes capable of giving unsaturated monomeric units, in particular conjugated dienes such as butadiene and isoprene, linear non-conjugated dienes such as trans 1,4-hexadiene, cis 1,4-hexadiene, 6-methyl-1,5-heptadiene, 3,7-dimethyl-1,6-octadiene, 11-methyl-1,10-dodecadiene, and cyclic non-conjugated dienes such as 5-ethylidene-2-norbornene.

In the case of polyenes other than non-conjugated alpha-omega-diolefins having 6 or more carbon atoms, these are preferably used in quantities of between 0 and 10 mol % as a second alpha-olefin comonomer.

A particular interesting embodiment of the present invention is constituted of copolymers of ethylene with propylene, 1-hexene or higher alpha-olefins.

The analysis of the distribution of the comonomer units in the copolymers of the invention has been carried out by means of $^{13}$C-NMR spectroscopy. The assignments were carried out as described by Randall in Macromol.Chem.Phys. 29, 201, 1989. The distribution of triads, in the case of ethylene/1-hexene, are calculated by the following relationship:

$$HHH=T_{\beta\beta} EHE=T_{\delta\delta} HHE=T_{\beta\delta} HEH=S_{\beta\beta} HEE=S_{\beta\delta} EEE=0.5(S_{\delta\delta}+0.5S_{\gamma\delta})$$

wherein EHE, HHE and HHH represent the sequence ethylene/1-hexene/ethylene, 1-hexene/1-hexene/ethylene and 1-hexene/1-hexene/1-hexene respectively in the copolymer. For the NMR nomenclature, see J. Carmen, R. A.

Harington, C. E. Wilkes, Macromolecules, 10, 537 (1977). The values are normalized. The higher the number of isolated 1-hexene units in the polymeric chain, the more the values of the ratio EHE/(EHE+HHE+HHH) become closer to the unit.

The number of 1-hexene sequences seems to be a function of the amount of 1-hexene units present in the chain.

The tables 2 and 3 refer to ethylene/1-hexene copolymers obtained with a process according to the present invention.

In particular, in table 3 there are reported the ratios EHE/(EHE+HHE+HHH) as a function of the molar percentage of 1-hexene in the chain for ethylene/1-hexene copolymers obtained with a process according to the present invention, in the presence of the above reported metallocene compounds.

In the case of ethylene/1-hexene, the reactivity ratio $r_1$ and the product of the reactivity ratios $r_1.r_2$ are calculated according to the following formulae as described in J. Uozomi, K. Soga, Mak. Chemie, 193, 823, (1992):

$$r_1=2[EE]/[EH]X$$

$$r_1.r_2=4[EE][HH]/[EH]^2$$

wherein X=[E]/[H] monomer molar ratio in the polymerization bath.

In the case of ethylene/propylene copolymers, the product of the reactivity ratios $r_1.r_2$, wherein $r_1$ is the reactivity ratio of propylene and $r_2$ that of ethylene, is calculated according to the following formula:

$$r_1.r_2=1+f(\chi+1)-(f+1).(\chi+1)^{1/2}$$

wherein f=ratio between moles of ethylene units and moles of propylene units in the copolymer, and $\chi$=(PPP +PPE)/EPE.

The molecular weight of the polymers can be varied by varying the type or the concentration of the catalyst components or using molecular weight regulators such as, for example, hydrogen.

Generally, the polymers of the present invention are endowed with a narrow molecular weight distribution. The molecular weight distribution is represented by the ratio $M_w/M_n$ which, for the polymers of the present invention, when the metallocene used is a pure isomer, is generally lower than 4, preferably lower than 3.5 and, more preferably, lower than 3.

The molecular weight distribution can be varied by using mixtures of different metallocene compounds or by carrying out the polymerization in several stages at different polymerization temperatures and/or different concentrations of the molecular weight regulators.

The polymers of the invention are generally soluble in common solvents, such as, for instance, chloroform, hexane, heptane, toluene and xylene.

The polymers of the invention are transformable into shaped articles by conventional thermoplastic material processing such as molding, extrusion, injection etc.

The following examples are given for illustrative purposes and are not intended to limit the scope and spirit of the invention.

EXAMPLES

General Procedures and Characterizations:
The following abbreviations are used:
THF=tetrahydrofuran
Et$_2$O=ethyl ether
NaOEt=sodium ethoxide
$^t$BuOK=potassium tert-butoxide
DMSO=dimethyl sulfoxide
DMF=N,N-dimethylformamide
BuLi=butyllithium All operations were performed under nitrogen by using conventional Schlenk-line techniques. Solvents were distilled from blue Na-benzophenone ketyl (Et$_2$O), CaH$_2$ (CH$_2$Cl$_2$), or Al-iBu$_3$ (hydrocarbons), and stored under nitrogen. BuLi (Aldrich) was used as received.

The $^1$H-NMR analyses of the metallocenes were carried out on a Varian VXR-400 spectrometer (CD$_2$Cl$_2$, referenced against the middle peak of the triplet of residual CHDCl$_2$ at 5.35 ppm). All NMR solvents were dried over P$_2$O$_5$ and distilled before use. Preparation of the samples was carried out under nitrogen using standard inert atmosphere techniques.

The $^{13}$C-NMR and $^1$H-NMR analyses of the polymers were carried out on a Bruker DPX 400 spectrometer operating at 400.13 MHz and 100.61 MHz respectively and were analyzed at 120° C. The powder polymer samples were dissolved in 1,1,2,2-tetrachloro-1,2-dideuteroethane (C$_2$D$_2$Cl$_4$) to give an 8% (wt./vol.) concentration. About 13000 transients were acquired with a 75° pulse and 15 seconds of delay between pulses.

Intrinsic Viscosity

The measurement were carried out in a tetrahydronaphthalene (THN) solution obtained by dissolving the polymer at 135° C. for 1 hour.

The melting points of the polymers (Tm) were measured by Differential Scanning Calorimetry (D.S.C.) on an DSC Mettler instrument, according to the following method. About 10 mg of sample obtained from the polymerization were cooled to −25° C. and thereafter heated at 200° C. with a scanning speed corresponding to 20° C. minute. The sample was kept at 200° C. for 5 minutes and thereafter cooled to 0° C. with a scanning speed corresponding to 20° C./minute. After standing 5 minutes at 0° C., the sample was heated to 200° C. at a rate of 10° C./min. In this second heating run, the peak temperature was taken as melting temperature ($T_m$) and the area as global melting hentalpy ($\Delta H_f$).

Size exclusion chromatography (SEC):
The analysis were performed by using a "WATERS 200" GPC, working at 135° C. with 1,2-dichlorobenzene (stabilized with BHT, 0.1 wt. %).

Preparation of the Ligand Precursors
Synthesis of 3,3'dibromo-2,2'-dithienylmethanol

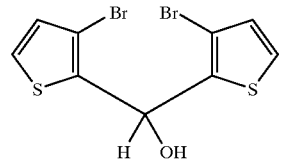

A 2.5 M solution of n-BuLi in hexane (24.30 mL, 60.76 mmol) was added dropwise at −20° C. to a solution of 15.00 g of 2,3-dibromothiophene (Aldrich, 98%, Mw=241.94, d=2.137, 60.76 mmol, n-BuLi:2,3-Br$_2$thiophene=1:1) in 90 mL of ether. The solution turned from pale yellow to yellow. After 1 h stirring at −20° C., 2.53 mL of ethylformate (Aldrich, 97%, Mw=74.08, d=0.917, 30.38 mmol, HCOOEt:2,3-Br$_2$thiophene=0.5:1) in 30 mL of ether was added dropwise. During the addition the solution turned from yellow to dark yellow. The reaction mixture was kept at −20° C. for 15 mm, then allowed to warm to room temperature and stirred for 20 h. The final pale orange suspension was poured at 0° C. into acidic water (1.65 g of $NH_4Cl$ in 75 mL of water), the organic layer was separated out and the water layer extracted with ether (3×25 mL). The organic layers were collected, dried over $Na_2SO_4$ and the solvents were removed under vacuum at 30–35° C. to give an orange oil (9.52 g), which was characterized by GC-MS analysis and $^1$H-NMR spectroscopy.

$^1$H NMR (δ, ppm, $CDCl_3$): 7.28 (d, 2H, J=5.29, CH); 6.95 (d, 2H, J=5.29, CH); 6.41 (s, 1H, CH); 2.86 (bs, 1H, CH).

m/z (%): 356 (23) [M$^+$+4], 354 (42) [M$^+$2], 352 (22) [M$^+$], 339 (10), 337 (18), 275 (10), 273 (10), 194 (11), 193 (23), 192 (11), 191 (100), 177 (32), 166 (10), 164 (10), 121 (17), 111 (14), 84 (33), 83 (15), 82 (26), 81 (14), 69 (11), 45 (33), 39 (15).

Synthesis of 3,3'-dibromo-2,2'-dithienylmethane

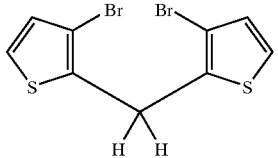

9.45 g of 3,3'-dibromo-2,2'-dithienylmethanol obtained as above described (20741/68A, Mw=354.09, 26.69 mmol considering starting material 100% pure) were dissolved into 85 mL of dichloromethane in a 250 mL three-necked bottom flask under nitrogen atmosphere and added at 0° C. of 4.26 mL of triethylsilane (Aldrich, Mw=116.28, d=0.728, 26.69 mmol). Then 2.06 mL of $CF_3COOH$ (Aldrich, Mw=114.02, d=1.48, 26.69 mmol) were added dropwise at 0° C. to the stirred mixture. During the addition, the reaction mixture turned from dark orange to dark red. It was kept at 0° C. for 15–20 min, then allowed to warm to room temperature and stirred for 3 h and 30 min at the same temperature. After cooling to 0° C., potassium carbonate (Fluka, 3.69 g, Mw=138.21, 26.69 mmol) was added to the dark red solution, the latter stirred for 30 min at room temperature and finally filtered on G4 frit. The residue on the frit was washed twice with $CH_2Cl_2$ (2×20 mL) until colourless, while the filtrate was dried under vacuum at 45° C. for 3 h to give a dark red oil (9.07 g), which was analysed by GC-MS analysis and $^1$H-NMR spectroscopy. Purity (by GC-MS)=79.9%. Yield of the pure product=80.3%. 3-bromo-2,2'-dithienylmethane (9.9% wt.) and hexaethyldisiloxane (6.2% wt.) were present as by-products. The product was used as such in the next step without further purification.

$^1$H NMR (δ, ppm, $CDCl_3$): 7.16 (d, 2H, J=5.38, CH); 6.94 (d, 2H, J=5.38, CH); 427 (s, 2H), $CH_2$).

m/z (%): 340 (28) [M$^+$+4], 338 (51) [M$^+$+2], 336 (26) [M$^+$], 259 (55), 257 (51), 179 (15), 178 (100), 177 (43), 89 (16), 45 (10).

Synthesis of 7H-cyclopenta[1,2-b:4,3-b']dithiophene

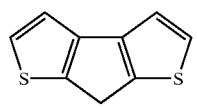

A 2.5 M solution of n-BuLi in hexane (21.30 mL, 53.25 mmol) was added dropwise at −50° C. to a solution of 8.99 g of 3,3'-dibromo-2,2'-dithienylmethane obtained as above described (20741/69A, Mw=338.09, 26.59 mmol) in 75 mL of ether under nitrogen atmosphere in a 250 mL flask. After 1 h stirring at −50° C., the dark brown dilithium suspension was added slowly to a suspension of 7.26 g of $CuCl_2$ (Aldrich, 98%, Mw=134.45, 52.92 mmol) in 50 mL of $Et_2O$.

The reaction mixture was kept at −50° C. for 30 mm, allowed to warm to −20° C. in 2 h 30 mm and then allowed to reach 0° C. in few minutes. Aliquots were taken after 30 mm at −50° C., at −20° C. and after 1 h at 0° C. to follow the reaction state by GC-MS analysis. It appeared that the $CuCl_2$ induced coupling reaction starts at −50° C. but proceeds slowly until 0° C. Only 10% wt. of 7H-cyclopenta[2,1-b:4,3-b']dithiophene was formed after 1 h at 0° C. After keeping at 0° C. for 1 h 30 mm, the reaction mixture was stirred overnight at room temperature and subsequently poured at 0° C. into 100 mL of an aqueous 2 M HCl solution. The resulting mixture was stirred for 15 mm at room temperature, filtered in order to remove the greyish precipitate of $Cu_2Cl_2$, the ether layer was separated out and the aqueous phase extracted with ether. The combined ethereal extracts were washed with HCl 2 M (100 mL), two times with $NaHCO_3$ aq. and finally with ether. The resulting organic phase (final volume=300 mL) was dried over $Na_2SO_4$ and the solvents removed in vacuo giving 3.16 g of a dark red oil, which was analysed by GC-MS analysis and $^1$H-NMR spectroscopy. The analysis showed the presence of the desired product together with dimers, trimers and tars. The crude product was added of 40 mL of ethanol and stirred for 1 h at room temperature. The yellow-orange extract was concentrated in vacuo at 55° C. for 4 h to give a dark orange oil (1.92 g), which crystallized by standing at 0° C. overnight.

Purity (by GC-MS)=ca. 50%. Yield of the pure product=20.2%.

$^1$H NMR (δ, ppm, $CDCl_3$): 7.30 (d, 2H, J=4.93, CH); 7.13 (d, 2H, J=4.93, CH); 3.80 (s, 2H), $CH_2$).

m/z (%): 180 (9) [M$^+$+2], 179 (16) [M$^+$+1], 178 (100) [M$^+$], 177 (92), 134 (13), 89 (7), 69 (6), 45 (6).

Synthesis of bis(3,5-dibromo-2-thienyl)methanol (or 3,3',5,5'-tetrabromo-2,2'-dithienyl carbinol)

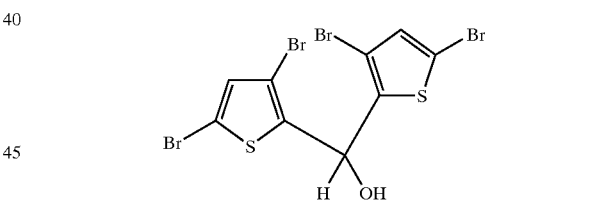

A solution of 31.35 g of 2,3,5-tribromothiophene (Lancaster, 98%, MW=320.84, 95.75 mmol) in 70 mL of ether was cooled to −78° C. and treated dropwise with 38.3 mL of a 2.5 M n-BuLi solution in hexane (95.75 mmol). The resulting mixture was allowed to warm to room temperature, stirred in additional 1 h and then added at 0÷−10° C. to a solution of 3.86 mL of ethylformate (Aldrich, 97%, MW=74.08, d=0.917, 46.35 mmol) in 20 mL of hexane, previously cooled to 0÷−10° C. At the end of the addition (~20 min) the reaction mixture was allowed to warm to room temperature and then refluxed for 1 h. The resulting mixture was quenched with 7.5 mL of water, the organic layer was separated out, dried over magnesium sulphate and the solvents evaporated off giving 23.2 g of a pale brown solid, which was analyzed by $^1$H NMR, $^{13}$C NMR, GC-MS. Purity=93.0%. Isolated yield towards ethylformate=90.9%. The title compound was analyzed by $^1$H NMR and $^{13}$C NMR spectroscopy.

Synthesis of 3,3',5,5'-tetrabromo-2,2'-dithienylmethane

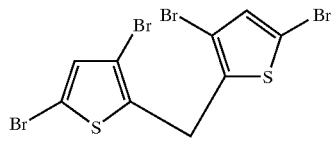

Trifluoroacetic acid (0.25 mL, Aldrich, 99%, MW=114.02, d=1.48, 3.24 mmol) was added at room temperature to a solution of 1.75 g of bis(3,5-dibromo-2-thienyl)methanol (93.0%, MW=511.90, 3.18 mmol) in 15 mL of methylene chloride containing 0.50 mL of triethylsilane (Aldrich, 99%, MW=116.28, d=0.728, 3.13 mmol). The resulting red solution was stirred for 1 h at room temperature, neutralized with solid potassium carbonate (0.4 g, MW=138.21, 2.89 mmol), filtered and evaporated off to give a pale red solid. Yield of crude product=100%. The title compound was analyzed by $^1$H NMR and $^{13}$C NMR spectroscopy.

Synthesis of 3,3'-dibromo-5,5'-dimethyl-2,2'-dithienylmethane

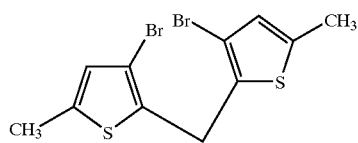

A precooled (−20° C.) 2.5 M solution of n-BuLi in hexane (41.1 mL, 102.75 mmol) was added at −20° C. to a solution of 25.48 g of 3,3',5,5'-tetrabromo-2,2'-dithienylmethane (MW=495.90, 51.38 mmol) in 100 mL of Et$_2$O. After 30 min stirring at −20° C., a precooled (−20° C.) ethereal (10 mL) solution of dimethyl sulphate (Aldrich, 9.72 mL, MW=126.13, d=1.333, 102.75 mmol) was added. The resulting black suspension was stirred for 45 min at −20° C.; the cooling bath was then removed and the flow of nitrogen stopped. A 4 N solution of sodium hydroxide (2.5 mL, 10 mmol) was added and the mixture vigorously stirred for 2 h at room temperature. The resulting reaction mixture was dried over magnesium sulphate, filtered, the residue on the frit washed twice with ether (to recover all the product) and the filtrate concentrated under reduced pressure at 40° C. for 2 h giving 17.8 g of a brown solid. Purity=87.8% (by GC-MS). Yield of pure product=83.1% (crude yield=94.6%). The title compound was analyzed by $^1$H NMR, $^{13}$C NMR and MS spectroscopy.

Synthesis of 2,5-dimethyl-7H-cyclopenta[1,2-b:4,3-b']dithiophene (or 2,5-dimethyl-7H-thieno[3',2':3,4]cyclopenta[b]thiophene)

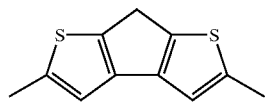

A solution of 0.1 mol of 3,3'-dibromo-5,5'-dimethyl-2,2'-dithienylmethane in 200 mL ether was treated with 0.23 mol of n-BuLi at −70° C. At the end of the addition, the reaction mixture was stirred for additional 30 min at the same temperature. Then 0.265 mol of CuCl$_2$ was added quickly. The resulting mixture was allowed to warm to room temperature and stirred for 12 h. The final suspension was poured into water, the organic layer was separated out and concentrated. The residue was recrystallized from ether. Yield 25%. The title compound was analyzed by $^1$H NMR and $^{13}$C NMR spectroscopy.

Synthesis of 3,3'-dibromo-5,5'-ditrimethylsilyl-2,2'-dithienylmethane

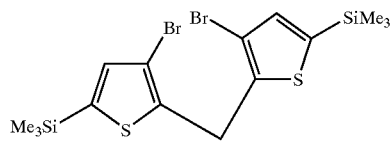

A 2.18 M solution of n-BuLi (65 mL, 141.7 mmol) was added at −70° C. to a solution of 34.8 g of 3,3',5,5'-tetrabromo-2,2'-dithienylmethane (70.2 mmol) in 150 mL of ether. The mixture was stirred for 30 min at the same temperature and then added of 35.5 mL of Me$_3$SiCl (280 mmol) in 65 mL of ether. The resulting mixture was allowed to warm to room temperature, the LiCl was filtered, and the mother solution was evaporated off to give an oil which represented the target compound in at least 95% purity. To this oil 50 mL of hexane was added and the resulting solution kept at −30° C. for 10 h. Big crystals were isolated, washed with cooled hexane and dried. Yield of recrystallized product 60%. The title compound was characterized by $^1$H-NMR and $^{13}$C-NMR spectroscopy.

Synthesis of 2,5-ditrimethylsilyl-7H-cyclopenta[1,2-b:4,3-b']dithiophene (or 2,5-dimethyltrimethylsilyl-7H-thieno[3',2':3,4]cyclopenta[b]thiophene)

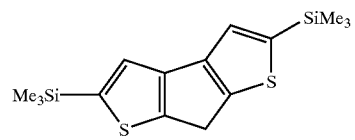

A solution of 0.1 mol of 3,3'-dibromo-5,5'-ditrimethylsilyl-2,2'-dithienylmethane in 200 mL ether was treated with 0.23 mol of n-BuLi at −70° C. At the end of the addition, the reaction mixture was stirred for additional 30 min at the same temperature. Then 0.265 mol of CuCl$_2$ was added quickly. The resulting mixture was allowed to warm to room temperature and stirred overnight. The resulting suspension was poured into water, the organic phase was separated out and concentrated. The residue was passed through a column packed with SiO$_2$ using hexane or a mixture hexane/ether as eluent. The resulting solution was evaporated off giving a crystalline or oily-crystalline solid which represented the desired product. Yield 50-60%. The crude product can be further purified in ether by filtration at 0° C. or by recrystallization from pentane. The title compound was characterized by $^1$H-NMR and $^{13}$C-NMR spectroscopy.

Synthesis of 3,3'-dibromo-5,5'-dihydroxyboryl-2,2'-dithienylmethane

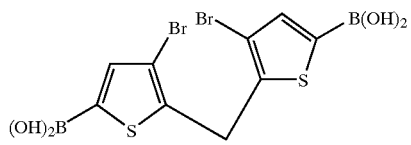

A 1.6 N solution of n-BuLi (100 ml, 160 mmol) was added to a solution of 39.6 g of 3,3',5,5'-tetrabromo-2,2'-dithienylmethane (79.8 mmol) in 150 mL ether at −70° C.

The mixture was stirred for 30 min at the same temperature and then added of 23.3 g of B(OMe)₃ (220 mmol) in 100 mL of ether. The reaction mixture was allowed to warm to room temperature. The resulting suspension was treated with 100 mL of a 10% aqueous HCl solution, the organic layer was separated out, washed twice with 50 mL of a 10% aqueous Na₂CO₃ solution, evaporated off and dried. The resulting solid which represented the crude di-boronic acid was used in the next step without further purification. The title compound was characterized by ¹H-NMR and ¹³C-NMR spectroscopy.

Synthesis of 3,3'-dibromo-5,5'-diphenyl-2,2'-dithienylmethane

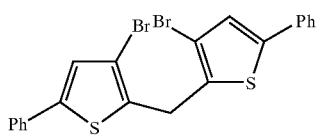

1.81 g of 3,3'-dibromo-5,5'-dihydroxyboryl-2,2'-dithienylmethane (3.76 mmol), 1.40 g of PhI (6.84 mmol), 0.15 g of PdCl₂(dppf)₂ (0.21 mmol), 120 mL of DMF and 8 mL of Et₃N were placed into the reaction flask and this mixture was stirred at 80° C. for 2 h. The resulting mixture was poured into a CH₂Cl₂/water two-phase system. The organic layer was collected, washed twice with 30 mL of 10% phosphoric acid, then with water and finally evaporated off The residue was passed through a column packed with SiO₂ using hexane/CH₂Cl₂=1/1 as eluent. The resulting solution was evaporated off, the residue washed with hexane and dried to give 0.6 g of diphenyl derivative. Yield 32%. The title compound was characterized by ¹H-NMR and ¹³C-NMR spectroscopy.

Synthesis of 2,5-diphenyl-7H-cyclopenta[1,2-b:4,3-b'] dithiophene (or 2,5-diphenyl -7H-thieno[3',2':3,4] cyclopenta[b]thiophene)

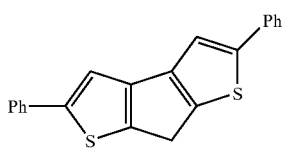

A 1.6 N n-BuLi solution (11.9 mL, 19 mmol) was added to a solution of 4.24 g of 3,3'-dibromo-5,5'-diphenyl-2,2'-dithienylnethane (8.65 mmol) in 50 mL of ether at −70° C. At the end of the addition, the reaction mixture was stirred for additional 30 min at the same temperature. Then 5.6 g of CuCl₂ (41.8 mmol) was added quickly. The resulting mixture was allowed to warm to room temperature and stirred overnight. The final suspension was poured into water, the organic phase was separated out and the solvent evaporated off. The residue was passed through a column packed with SiO₂ using hexane/CH₂Cl₂=4/1 as eluent. The resulting solution was evaporated off to leave a residue, which was washed with hexane and dried to give 1.1 g of crystalline solid. Yield 38%. The title compound was characterized by ¹H-NMR and ¹³C-NMR spectroscopy.

Synthesis of 2-methyl-4-bromo-thiophene

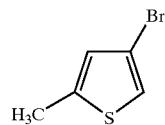

1 mol of 2-thiophenecarboxaldehyde was added to 2.5 mol of pulverized AlCl₃ under stirring keeping the temperature below 40° C. At the end of the addition the liquid complex was solidified; then 1.2 mol of bromine was carefully added dropwise under stirring. When the addition was complete, stirring became impossible because of the mixture solidified completely. This solid substance was poured into a mixture of ice (0.5 Kg) and hydrochloric acid (100 mL, 32%), then 300 mL of CH₂Cl₂ was added. The organic phase was separated out and the solvent removed. The resulting substance (4-bromo-2-thiophenecarboxaldehyde) was dissolved in 700 mL of di(ethylene glycol) and the so-obtained solution was treated with 5.5 mol of hydrazine hydrate. The resulting mixture was refluxed for 30 min. After cooling up to room temperature, 2.75 mol of potassium hydroxide was added. After the gas evolution was over, the distillation was started and the fraction before 150° C. was collected. This fraction represented the mixture of water and desired product: the organic layer was separated out and distilled at 60° C./10 torr. Yield 52%.

¹H NMR (δ in ppm, CDCl₃): 6.99 (d, 1H, H$_α$); 6.69 (q, 1H, H$_β$); 2.48 (d, 3H, CH₃).

Synthesis of 2-methyl-4-formyl-thiophene

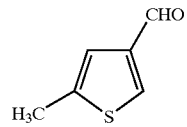

To a stirred solution of 44.26 g of 2-methyl-4-bromo-thiophene (0.25 mol) in 300 mL of ether, 164 mL of a 1.6 M solution of n-BuLi (0.26 mol) was added at −70° C. The resulting solution was kept under stirring at −60 to −70° C. for 30 mm and then was treated with 27.4 g of dimethylformamide (0.37 mol) in 100 mL of ether. The mixture was allowed to warm to room temperature, then neutralized with 10% aqueous solution of NH₄Cl, washed with 10% aqueous solution of H₃PO₄ and finally with water up to neutral pH. The organic phase was collected, evaporated off and distilled at 110° C./10 mmHg. Yield 22.3 g (71%). The title compound was characterized by ¹H-NMR spectroscopy.

Synthesis of 2,2'-dimethyl-4,4'-dithienylmethane

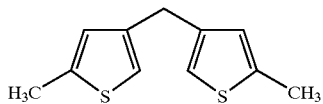

113 mL of 1.6 M n-BuLi solution (0.18 mol) was added to a solution of 31.3 g of 2-methyl-4-bromo-thiophene (0.177 mol) in 150 mL of ether at −70° C. under stirring. The resulting solution was kept under stirring at −60 to −70° C. for 30 mm and then was added of 22.3 g of 2-methyl-4-formyl-thiophene (0.177 mol) in 100 mL of ether. The mixture was allowed to warm to room temperature, then neutralized with 10% aqueous solution of NH₄Cl and washed with water. The organic phase was separated out and evaporated off (crude bis(2-methyl-4-thienyl)methanol or 2,2'-dimethyl-4,4'-dithienyl carbinol).

A suspension of 35.5 g of AlCl$_3$ (0.266 mol) in 100 mL of ether was added slowly to a suspension of 10 g of LiAlH$_4$ (0.266 mol) in 100 mL of ether. The resulting mixture was treated with the solution of the carbinol obtained as above described in 100 mL ether. Then the reaction mixture was refluxed for additional 1 h, cooled up to room temperature and finally added of 100 mL of ethyl acetate. After it was treated with 300 mL of water and 300 mL of ether. The organic phase was collected, washed with water, dried over MgSO$_4$ and evaporated off. The residue was distilled at 90 to 110° C./0.5 mmHg. Yield 23.2 g (63%). The title compound was characterized by $^1$H-NMR spectroscopy.

Synthesis of 2,6-dimethyl-4H-cyclopenta[2,1-b:3,4-b']dithiophene (or 2,6-dimethyl-4H-thieno[3',2':2,3]cyclopenta[b]thiophene)

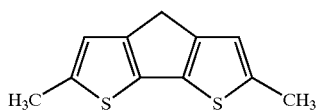

1.04 g of 2,2'-dimethyl-4,4'-dithienylmethane (5 mmol) was dissolved in 30 mL of ether and added of 9 mL of 1.6 M solution of n-BuLi (14.4 mmol) and of 1.74 g of TMEDA (15 mmol) at −70° C. under stirring. The resulting mixture was allowed to warm to room temperature, stirred for 1 h, then cooled again to −70° C. and treated with 2.7 g of CuCl$_2$ (20 mmol). The resulting reaction mixture was allowed to warm to room temperature and added of 30 mL of water. The organic phase was collected and passed through a column packed with silica gel. The resulting solution was evaporated off to give 0.34 g of the product. Yield 34%. The title compound was characterized by $^1$H-NMR spectroscopy.

Synthesis of 2-ethyl-4-bromo-thiophene

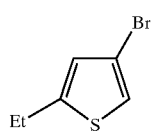

1 mol of acethylthiophene dissolved in 250 mL of CHCl$_3$ was added slowly to a suspension of 2.5 mol of AlCl$_3$ in 1000 mL of CHCl$_3$ under stirring keeping the temperature below 40° C. At the end of the addition, 1.2 mol of Br$_2$ was carefully added dropwise under stirring. The resulting mixture was stirred overnight and then was poured into a mixture of ice (0.5 Kg) and hydrochloric acid (100 mL, 32%). The organic phase was isolated and the solvent was removed. The resulting substance was dissolved in 700 mL of diethyleneglicole and the so-obtained solution was treated with 5.5 mol of 100% hydrazine hydrate. The resulting mixture was refluxed for 30 min. After cooling to room temperature, 2.75 mol of KOH were added. When the gas evolution was ended, the product was distilled. The fraction under the temperature of 150° C. was collected. This fraction represented a mixture of water and product. The organic layer was collected and distilled at 80° C./10 torr. Yield 45%.

$^1$H-NMR (δ, ppm, CDCl$_3$, 20° C.): 7.05 (d, 1H, H5); 6.76 (q, 1H, H3); 2.86 (q, 2H, CH$_2$); 1.33 (t, 3H, CH$_3$).

Synthesis of 3,3'-dibromo-5,5'-diethyl-2,2'-dithienylmethane

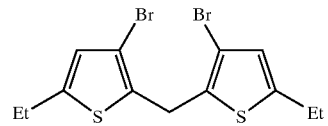

The 2-ethyl-4-bromo-thiophene obtained in the previous step was dissolved into 120 mL of AcOH and was treated with a mixture of 6.1 mL of H$_2$SO$_4$ and 9.1 mL (MeO)$_2$CH$_2$. The reaction mixture was stirred overnight, then was washed with 300 mL of water and finally extracted with CH$_2$Cl$_2$. The organic phase was separated out and dried under reduced pressure. The residue was passed throught a column packed with Al$_2$O$_3$ using hexane as eluent. The solvent was removed and the desired product was obtained as yellow oil. Yield 90%.

$^1$H-NMR (δ, ppm, CDCl$_3$, 20° C.): 6.68 (m, 2H, CH); 4.20 (s, 2H, CH$_2$ bridge); 2.80 (q, 4H, CH$_2$); 1.30 (t, 6H, CH$_3$).

Synthesis of 2,5-diethyl-7H-cyclopenta[1,2-b:4,3-b']-dithiophene

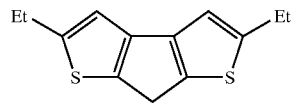

A solution of 0.1 mol of 3,3'-dibromo-5,5'-diethyl-2,2'-dithienylmethane in 200 mL of ether was treated at −70° C. with 0.23 mol of n-BuLi. At the end of the addition, the mixture was stirred for additional 30 min at the same temperature. The white precipitate of the dilithium salt was formed. Then 0.265 mol of CuCl$_2$ was added at −70° C. quickly. The reaction mixture was allowed to warm to room temperature and stirred for 12 h. The resulting suspension was poured into water, the organic phase was separated out and concentrated. The residue was recrystallized from ether. Yield 25%.

$^1$H-NMR (δ, ppm, CDCl$_3$, 20° C.): 6.86 (m, 2H, CH); 3.74 (s, 2H, CH$_2$); 2.98 (q, 4H, CH$_2$); 1.38 (t, 6H, CH$_3$).

Example 1

Synthesis of isopropylidene{(cyclopentadienyl)-7-(cyclopenta[1,2-b:4,3-b']-dithiophene)}zirconium dichloride [Z$_s$-50]

It was carried out as described in the Example 6 of WO 98/22486.

Example 2

Synthesis of 2,2-(cyclopentadienyl)-7-(2,5-dimethyl-cyclopentadienyl-[1,2-b:4,3-b']-dithiophene)propane

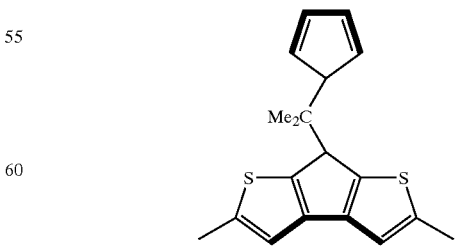

A solution of 1.03 g (5 mmol) of 2,5-dimethyl-cyclopentadiene-[1,2-b:4,3-b']-dithiophene the in 20 ml ether was treated at −70° C. with 3.13 ml of 1.6M BuLi (5 mmol). The resulting mixture was stirred in additional 30 min at 0° C., cooled again to −70° C. and then was treated with 0.53 g (5 mmol) 6,6-dimethylfulvene in 10 ml ether. The mixture was allowed to warm to r.t. then was treated with saturated aqueous solution of $NH_4Cl$. The organic phase was isolated, dried and evaporated off. The residue was recrystallyzed from hexane. Yield 1.1 g (64%).

The title compound was characterized by $^1$H-NMR spectroscopy.

Preparation of isopropylidene(cyclopentadienyl)-7-(2,5-dimethyl-cyclopentadienyl-[1,2-b:4,3-b']-dithiophene) zirconium dichloride [$Z_s$-0]

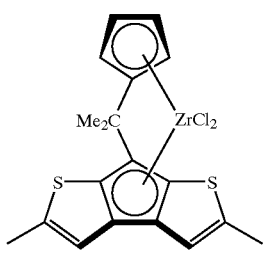

A suspension of 1.0 g(3.22 mmol) of 2,2-(cyclopentadienyl)-7-(2,5-dimethyl-cyclopentadienyl-[1,2-b:4,3-b']-dithiophene)propane in 20 ml ether was treated with 4.1 ml (6.0 mmol) 1.6M BuLi at −70° C. The mixture was allowed to warm to 0° C. and then was treated with 0.75 g (3.2 mmol) $ZrCl_4$. The reaction mixture was stirred at reflux within 3 h, then the yellow precipitate was filtered, washed twice with ether, dried and then recrystallyzed from $CH_2Cl_2$. Yield 1.37 g (90%).

The title compound was characterized by $^1$H-NMR and $^{13}$C-NMR spectroscopy.

Synthesis of 2,2-(3-methyl-cyclopentadienyl)-7-(2,5-dimethyl-cyclopenta[1,2-b:4,3-b']-dithiophene)propane

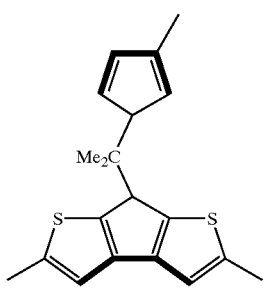

3.13 mL of a 1.6 M solution of n-BuLi (5 mmol) was added at −70° C. to a solution of 1.03 g (5 mmol) of 2,5-dimethyl-7H-cyclopenta[1,2-b:4,3-b']-dithiophene in 20 mL of ether. The resulting mixture was stirred for additional 30 min at 0° C., then cooled again to −70° C. and treated with 0.6 g (5 mmol) of 3,6,6-trimethylfulvene in 10 mL of ether. The reaction mixture was allowed to warm to room temperature and then treated with a saturated aqueous solution of $NH_4Cl$. The organic phase was isolated, dried over $MgSO_4$ and concentrated. The residue was recrystallized from hexane. Yield 1.0 g (62%). The title compound was characterized by $^1$H-NMR spectroscopy.

Synthesis of isopropylidene{(3-methyl-cyclopentadienyl)-7-(2,5-dimethyl-cyclopenta[1,2-b:4,3-b']-dithiophene)}zirconium dichloride [$Z_s$-1]

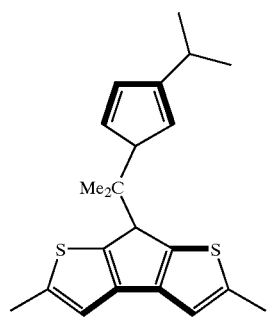

2.3 mL of 1.6 M n-BuLi solution (3.7 mmol) was added at −70° C. to a suspension of 0.6 g (1.85 mmol) of 2,2-(3-methyl-cyclopentadienyl)-7-(2,5-dimethyl-cyclopenta[1,2-b:4,3-b']-dithiophene)propane in 20 mL of ether. The mixture was allowed to warm to 0° C. and then was treated with 0.43 g (1.85 mmol) of $ZrCl_4$. The reaction mixture was refluxed under stirring for 3 h, then the yellow precipitate was filtered, washed twice with ether, dried and finally recrystallized from $CH_2Cl_2$. Yield 0.72 g (80%). The title compound was characterized by $^1$H-NMR spectroscopy.

Example 3

Synthesis of isopropylidene{(3-methyl-cyclopentadienyl)-7-(2,5-dimethyl-cyclopenta[1,2-b:4,3-b']-dithiophene)}hafnium dichloride [HS-1]

2.5 mL of 1.6 M n-BuLi solution (4.0 mmol) was added at −70° C. to a suspension of 0.65 g (2.0 mmol) of 2,2-(3-methyl-cyclopentadienyl)-7-(2,5-dimethyl-cyclopenta[1,2-b:4,3-b']-dithiophene)propane in 20 mL of ether. The mixture was allowed to warm to 0° C. and then was treated with 0.64 g (2.0 mmol) of $HfCl_4$. The reaction mixture was refluxed under stirring for 3 h, then the yellow precipitate was filtered, washed twice with ether, dried and finally recrystallized from $CH_2Cl_2$. Yield 0.48 g (42%). The title compound was characterized by $^1$H-NMR spectroscopy.

Example 4

Synthesis of 2,2-(3-isopropyl-cyclopentadienyl)-7-(2,5-dimethyl-cyclopenta [1,2-b:4,3-b']-dithiophene)propane 3.13 mL of a 1.6 M solution of n-BuLi (5 mmol) was added at −70° C. to a solution of 1.03 g (5 mmol) of 2,5-dimethyl-7H-cyclopenta[1,2-b:4,3-b']-dithiophene in 20 mL of ether. The resulting mixture was stirred for additional 30 min at 0° C., then cooled again to −70° C. and treated with 0.74 g (5 mmol) of 3-isopropyl-6,6-dimethylfulvene in 10 mL of ether. The reaction mixture was allowed to warm to room temperature and then treated with a saturated aqueous solution of NH$_4$Cl. The organic phase was isolated, dried over MgSO$_4$ and concentrated. The residue was recrystallized from hexane. Yield 0.85 g (48%).

The title compound was characterized by $^1$H-NMR spectroscopy.

Synthesis of isopropylidene{(3-isopropyl-cyclopentadienyl)-7-(2,5-dimethyl-cyclopenta[1,2-b:4,3-b']-dithiophene)}zirconium dichloride [Z$_s$-2]

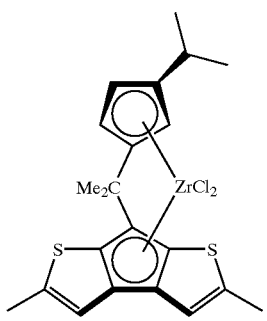

3.75 mL of 1.6 M n-BuLi solution (6.0 mmol) was added at −70° C. to a suspension of 1.06 g (3.0 mmol) of 2,2-(3-isopropyl-cyclopentadienyl)-7-(2,5-dimethyl-cyclopenta[1,2-b:4,3-b']-dithiophene)propane in 20 mL of ether. The mixture was allowed to warm to 0° C. and then was treated with 0.7 g (3.0 mmol) of ZrCl$_4$. The reaction mixture was refluxed under stirring for 3 h, then the yellow precipitate was filtered, washed twice with ether, dried and finally recrystallized from CH$_2$Cl$_2$. Yield 1.24 g (80%). The title compound was characterized by $^1$H-NMR spectroscopy.

Example 5

Synthesis of 2,2-(3-tert-butyl-cyclopentadienyl)-7-(2,5-dimethyl-cyclopenta[1,2-b:4,3-b']-dithiophene)propane

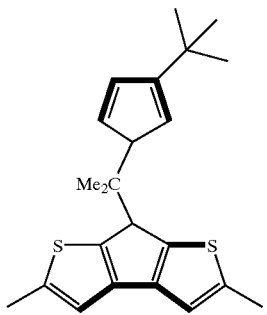

3.13 mL of a 1.6 M solution of n-BuLi (5 mmol) was added at −70° C. to a solution of 1.03 g (5 mmol) of 2,5-dimethyl-7H-cyclopenta[1,2-b:4,3-b']-dithiophene in 20 mL of ether. The resulting mixture was stirred for additional 30 min at 0° C., then cooled again to −70° C. and treated with 0.81 g (5 mmol) of 3-tert-butyl-6,6-dimethylfulvene in 10 mL of ether. The reaction mixture was allowed to warm to room temperature and then treated with a saturated aqueous solution of NH$_4$Cl. The organic phase was isolated, dried over MgSO$_4$ and concentrated. The residue was recrystallized from hexane. Yield 0.94 g (51%). The title compound was characterized by $^1$H-NMR spectroscopy.

Synthesis of isopropylidene{(3-tert-butyl-cyclopentadienyl)-7-(2,5-dimethyl-cyclopenta[1,2-b:4,3-b']-dithiophene)}zirconium dichloride [Z$_s$-3]

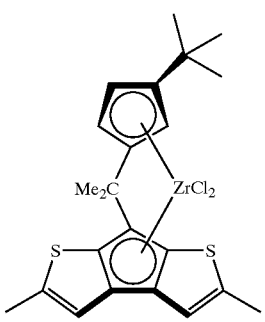

3.75 mL of 1.6 M n-BuLi solution (6.0 mmol) was added at −70° C. to a suspension of 1.11 g (3.0 mmol) of 2,2-(3-tert-butyl-cyclopentadienyl)-7-(2,5-dimethyl-cyclopenta[1,2-b:4,3-b']-dithiophene)propane in 20 mL of ether. The mixture was allowed to warm to 0° C. and treated with 0.7 g (3.0 mmol) of ZrCl$_4$. The reaction mixture was refluxed under stirring for 3 h, then the yellow precipitate was filtered, washed twice with ether, dried and finally recrystallized from CH$_2$Cl$_2$. Yield 1.27 g (80%). The title compound was characterized by $^1$H-NMR spectroscopy.

Example 6

Preparation of isopropylidene(3-tertbutylcyclopentadienyl)-7-(cyclopentadienyl-[1,2-b:4,3-b']dithiophene)zirconium dichloride [Z$_s$-51]

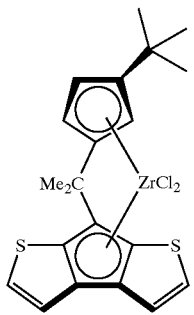

It was carried out as described in the Example 9 of WO 98/22486

Example 7

Synthesis of 1-methyl-3-phenyl-1,3-cyclopentadiene

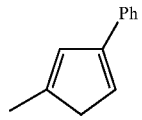

A solution of 25 g (0.26 mol) of 3-methyl-2-cyclopenten-1-one in 100 mL of ether was added at −78° C. under argon atmosphere to a solution of phenyl litium in 200 mL of ether, previous prepared from 5.76 g (0.83 mol) of lithium and 44 mL (0.42 mol) of bromobenzene. The reaction mixture was stirred for 4 h and then treated with a 10% aq. solution of NH$_4$Cl. The organic phase was collected, washed with water, dried over MgSO$_4$ and concentrated. The residue was distilled at 54° C./1 mmHg. Yield 24.37 g (60%).

$^1$H-NMR (δ, ppm, CD$_3$COCD$_3$): 7.60–7.10 (m, 5H, CH); 6.80 (d, 1H, CH); 6.00 (m, 1H, CH); 3.00 (s, 2H, CH$_2$); 1.98 (q, 3H, CH$_3$).

Synthesis of 1-methyl-3-phenyl-6,6-dimethylfulvene

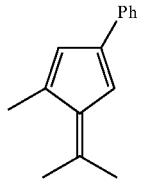

A solution of 1-methyl-3-phenyl-1,3-cyclopentadiene (15.62 g, 0.1 mol) in 100 mL of ethanol was treated at low temperature with 8.6 mL (0.12 mol) of acetone and 9.7 mL (0.12 mol) of pyrrolidine. The resulting solution was kept below room temperature overnight. Then the reaction mixture was neutralized with a 10% aq. solution of H$_3$PO$_4$, extracted with hexane (3×50 mL) and washed with water until neutral pH. The organic phase was separated out, dried over MgSO$_4$ and concentrated. The residue was distilled at 85° C./10 mmHg. Yield 5.89 g (30%). The desired title compound was characterized by $^1$H-NMR. The Z$_s$,14-ligand synthesis was carried out by following the same procedure above described for Z$_s$,17-ligand, by using 1-methyl-3-phenyl-6,6-dimethylfulvene instead of 1methyl-3-isopropyl-6,6-dimethylfulvene and 2,5-ditrimethylsilyl-7H-cyclopenta[1,2-b:4,3-b']dithiophene instead of MeTh$_2$Cp.

Synthesis of isopropilydene{(2-methyl-4-phenyl-cyclopentadienyl)-7-(2,5-trimethylsilylcyclopenta[1,2-b:4,3-b']-dithiophene)}zirconium dichloride [Z$_s$-14]

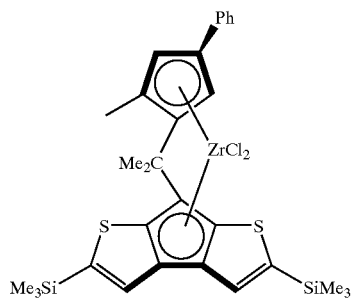

A suspension of 2.0 g (3.85 mmol) of 2,2-(2-methyl-4-phenyl-1-cyclopentadienyl)-7-(2,5-trimethylsilylcyclopenta[1,2-b:4,3-b']-dithiophene)propane in 50 mL of ether was treated at −70° C. with 4.8 mL of a 1.6 M n-BuLi solution (7.71 mmol). After the addition, the reaction mixture was allowed to warm to 0 C. and added of 0.90 g (3.85 mmol) of ZrCl$_4$. The resulting mixture was allowed to reach room temperature and stirred overnight. Then the brown precipitate obtained was filtered, washed twice with ether, dried and finally recrystallyzed from CH$_2$Cl$_2$. Yield 1.82 g (70%).

$^1$H-NMR (δ, ppm, CD$_2$Cl$_2$): 7.34 (s, 2H, CH); 7.32–7.12 (m, 5H, CH); 6.62 (d, 1H, CH); 6.26 (d, 1H, CH); 2.50 (s, 3H, CH$_3$); 2.30 (s, 3H, CH$_3$); 2.10 (s, 3H, CH$_3$); 0.36 (s, 9H, Si(CH$_3$)$_3$); 0.32 (s, 9H, Si(CH$_3$)$_3$).

Example 8

Synthesis of 2,2-(3-isopropyl-cyclopentadienyl)-7-(cyclopenta[1,2-b:4,3-b']-dithiophene)propane

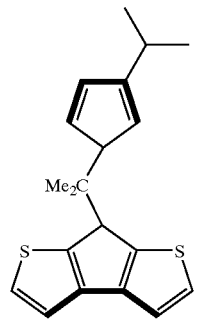

3.13 mL of 1.6 M solution of n-BuLi (5 mmol) was added to a solution of 0.89 g (5 mmol) of the 7H-cyclopenta[1,2-b:4,3-b']dithiophene in 20 mL of THF at −70° C. The resulting mixture was stirred for additional 30 min at 0° C., then cooled again to −70° C. and treated with 0.74 g (5 mmol) of 3-isopropyl-6,6-dimethylfulvene in 10 mL of ether. The reaction mixture was allowed to warm to room temperature and then treated with a saturated aqueous solution of NH$_4$Cl. The organic phase was isolated, dried over MgSO$_4$ and concentrated. The residue was passed through a column packed with silica gel using hexane as eluent (R$_f$=0.8). Yield 1.05 g (64%). The title compound was characterized by $^1$H-NMR spectroscopy.

Synthesis of isopropylidene(3-isopropyl-cyclopentadienyl)-7-(cyclopenta[1,2-b:4,3-b']-dithiophene)zirconium dichloride [Z$_s$-16]

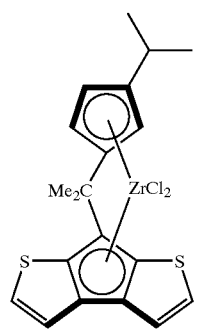

A solution of 1.05 g (3.22 mmol) of 2,2-(3-isopropyl-cyclopentadienyl)-7-(cyclopenta[1,2-b:4,3-b']-dithiophene)propane in a mixture of 10 mL of ether and 60 mL of hexane was treated with 4.1 mL (6.6 mmol) of a 1.6 M n-BuLi solution at −70° C. The mixture was allowed to warm to 0° C. and treated with 0.75 g (3.2 mmol) of ZrCl$_4$. The resulting reaction mixture was refluxed under stirring for 3 h, then the yellow precipitate was filtered, washed twice with hexane, dried and finally recrystallized from CH$_2$Cl$_2$/hexane. Yield 0.32 g (21%). The title compound was characterized by 1H-NMR spectroscopy.

Example 9
Synthesis of 3,6,6-trimethylfulvene

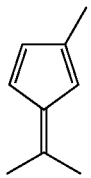

A solution of 2-methyl-1,3-cyclopentadiene (125 g, 1.56 mol) in 1.2 L of ethanol was treated at low temperature with 126 mL (1.72 mol) of acetone and 142 mL (1.72 mol) of pyrrolidine. The resulting solution was kept below room temperature overnight. Then the reaction mixture was neutralized with a 10% aq. solution of $H_3PO_4$, extracted with hexane (3×150 mL) and washed with water until neutral pH. The organic phase was separated out, dried over $MgSO_4$ and concentrated. The residue was distilled at 70° C./60 mmHg. Yield 112.6 g (60%).

$^1$H NMR (δ, ppm, $CDCl_3$): 6.53 (dd, 1H, CH); 6.35 (dd, 1H, CH); 6.20 (m, 1H, CH); 2.17 (s, 3H, $CH_3$); 2.16 (s, 3H, $CH_3$); 2.09 (s, 3H, $CH_3$).

Synthesis of 3-isopropyl-1-methyl-1,3-cyclopentadiene

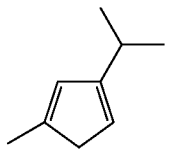

A solution of 24 g (0.2 mol) of 3,6,6-trimethylfulvene in 100 mL of ether was added at −78° C. under argon atmosphere to a solution of 7.59 g (0.2 mol) of lithium aluminium hydride in 200 mL of ether. The reaction mixture was allowed to warm to room temperature, stirred for 2 h and then treated with a 10% aq. solution of $NH_4Cl$. The organic phase was collected, washed with water, dried over $MgSO_4$ and concentrated. The residue was distilled at 63° C./50 mmHg. Yield 15.88 g (65%).The desired title compound was characterized by $^1$H-NMR.

Synthesis of 1-methyl-3-isopropyl-6,6-dimethylfulvene

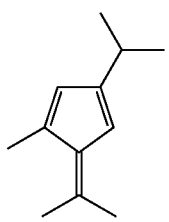

3-isopropyl-1methyl-1,3-cyclopentadiene (39 g, 0.32 mol) was added at low temperature to a suspension of 12.8 g (0.32 mol) of sodium hydroxide in 200 mL of dry THF. After 30 min stirring, the reaction mixture was treated with 23.8 mL (0.32 mol) of acetone. The resulting solution was kept below room temperature overnight. Then the resulting mixture was neutralized with a 10% aq. solution of $H_3PO_4$, extracted with hexane (3×100 mL) and washed with water until neutral pH. The organic phase was separated out, dried over$MgSO_4$ and concentrated. The residue was distilled at 80° C./10 mmHg. Yield 25.96 g (50%).

$^1$H NMR (δ, ppm, $CDCl_3$): 6.21 (m, 1H, CH); 6.05 (d, 1H, CH); 2.67 (m, 1H, CH); 2.24 (s, 3H, $CH_3$); 2.21 (s, 3H, $CH_3$); 2.20 (s, 3H, $CH_3$); 1.26 (s, 3H, $CH_3$); 1.28 (s, 3H, $CH_3$).

Synthesis of 2,2-(2-methyl-4-phenyl-cyclopentadienyl)-7-(2,5-dimethyl-cyclopenta[1,2-b:4,3-b']dithiophene)propane

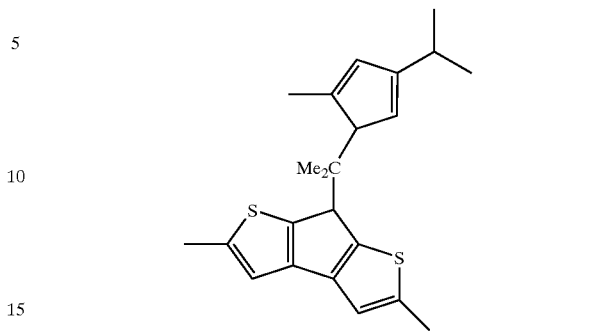

A 1.6 M solution of n-BuLi (6.25 mL, 10 mmol) was added at −70° C. to a suspension of 2.06 g (10 mmol) of 2,5-dimethyl-7H-cyclopenta[1,2-b:4,3-b']-dithiophene in 100 mL of ether. At the end of the addition, the mixture was allowed to warm to room temperature and stirred for additional 50 min at the same temperature. The resulting reaction mixture was treated at −70° C. with a solution of 0.74 g (5 mmol) of 1-methyl-3-isopropyl-6,6-dimethylfulvene, then was allowed to warm to room temperature and stirred overnight. The final mixture was poured into 100 mL of a 10% aq. solution of $NH_4Cl$ and extracted with hexane (2×50 mL). The organic phase was collected, washed with water, dried over$MgSo_4$ and evaporated off. The residue was passed through a column packed with $SiO_2$ by using hexane as eluent. The resulting solution was dried giving the crystalline product. Yield 1.5 (41% based on starting $MeTh_2Cp$).

Synthesis of isopropilydene{(2-methyl-4-isopropyl-cyclopentadienyl)-7-(2,5-dimethyl-cyclopenta[1,2-b:4,3-b']-dithiophene)}zirconium dichloride[$Z_s$-17]

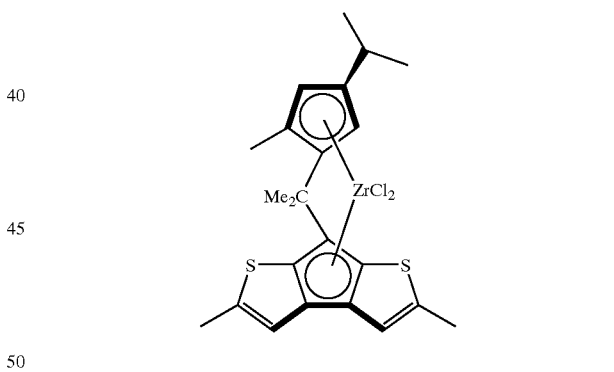

A suspension of 1.11 g (3 mmol) of 2,2-(2-methyl-4-isopropyl-1-cyclopentadienyl)-7-{(2,5-dimethyl-cyclopenta[1,2-b:4,3-b']dithiophene)}propane in 10 mL of ether and 50 mL of hexane was treated at −70° C. with 3.8 mL of a 1.6 M n-BuLi solution (6.1 mmol). After the addition, the reaction mixture was allowed to warm to 0° C. and added of 0.75 g (3.2 mmol) of $ZrCl_4$. The resulting mixture was allowed to reach room temperature and stirred overnight. Then the yellow precipitate obtained was filtered, washed twice with ether, dried and finally recrystallyzed from $CH_2Cl_2$.

Yield 1.43 g (90%).

$^1$H-NMR (δ, ppm, $CD_2Cl_2$): 6.88 (m, 1H, CH); 6.80 (m, 1H, CH); 6.10 (d, 1H, CH); 5.58 (d, 1H, CH); 2.78 (m, 1H, CH); 2.58 (m, 3H, $CH_3$); 2.56 (d, 3H, $CH_3$); 2.40 (s, 3H, $CH_3$); 2.18 (s, 3H, $CH_3$); 1.96 (s, 3H, $CH_3$); 1.14 (d, 3H, $CH_3$); 1.08 (d, 3H, $CH_3$).

Example 10
Synthesis of Benzofulvene

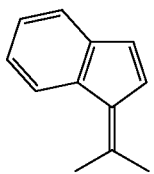

Indene (44.1 g, 0.38 mol) was added at 0° C. to a suspension of 20.0 g (0.50 mol) of sodium hydroxide in 100 mL of dry THF. After 30 min stirring, the reaction mixture was treated at the same temperature with 55.1 mL (0.75 mol) of acetone. The resulting mixture was then allowed to warm to room temperature and stirred overnight. The final mixture was neutralized with a 10% aq. solution of $H_3PO_4$, extracted with hexane (3×100 mL) and washed with water until neutral pH. The organic phase was separated out, dried over $MgSO_4$ and concentrated. The residue was distilled at 105° C./10 mmHg. Yield 29.6 g (50%).

$^1$H NMR (δ, ppm, $CD_3COCD_3$): 7.76 (m, 1H, CH); 7.34 (m, 1H, CH); 7.20 (m, 2H, CH); 6.90 (d, 1H, CH); 6.80 (d, 1H, CH); 2.40 (s, 3H, $CH_3$); 2.26 (s, 3H, $CH_3$).

The $Z_s$21-ligand synthesis was carried out by following the same procedure above described for $Z_s$17-ligand, by using benzofulvene instead of 1-methyl-3-isopropyl-6,6-dimethylfulvene.

Synthesis of isopropylidene{(1-indenyl)-7-(2,5-dimethyl-cyclopenta[1,2-b:4,3-b']-dithiophene)}zirconium dichloride [$Z_s$-21]

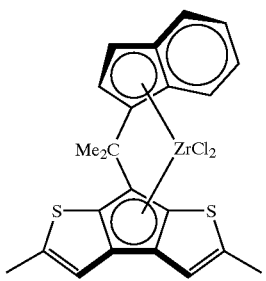

A suspension of 0.95 g (2.62 mmol) of 2,2-(1-indenyl)-7-{(2,5-dimethyl-cyclopenta[1,2-b:4,3-b']dithiophene)}propane in 10 mL of ether and 50 mL of hexane was treated at −70° C. with 3.6 mL of a 1.6 M n-BuLi solution (5.76 mmol). After the addition, the reaction mixture was allowed to warm to 0° C. and added of 0.67 g (2.88 mmol) of $ZrCl_4$. The resulting mixture was allowed to reach room temperature and stirred overnight. Then the brightly red precipitate obtained was filtered, washed twice with ether, dried and finally recrystallyzed from $CH_2Cl_2$.

Yield 0.96 g (70%). The desired title compound was characterized by $^1$H-NMR.

Polymerization

Methylalumoxane (MAO)

A commercial (Witco) 10% toluene solution was dried in vacuum until a solid, glassy material was obtained which was finely crushed and further treated in vacuum until all volatiles were removed (4–6 hours, 0.1 mmHg, 50° C.) to leave a white, free-flowing powder.

Tris(2,4,4-trimethyl-pentyl)aluminum (TIOA)

A commercial (Witco) sample was used diluted to a 1 M solution in the indicated solvent.

Preparation of TIOAO 5 ml of toluene and 3.5 mmol (3.5 ml) of TIOA solution (1 M in hexane) are introduced in a Schlenk tube. Then 1.75 mmol (31.5 μl) of $H_2O$ are added, and the resultant solution is stirred for 10 minutes at room temperature.

Polymerization Example 1 to 6
Ethylene Polymerization in a Glass Autoclave

Ethylene polymerization under standard conditions was performed in a 200 ml glass autoclave, provided with magnetic stirrer, temperature indicator and feeding line for the ethylene. It was purified and fluxed with ethylene at 35° C. 90 ml of hexane were introduced at room temperature. The catalytic system was prepared separately in 10 ml of hexane by consecutively introducing the Aluminum alkyl, MAO or TIOA/water (Al/H2O=2.1), and after 5 minutes of stirring, the metallocene solved in toluene (the lowest amount as possible). After 5 minutes of stirring the solution was introduced into the autoclave under ethylene flow. The reactor was closed, the temperature risen to 80° C. and pressurized with ethylene to 4.6 bar. The total pressure was kept constant by feeding ethylene. After the time indicated in Table 1, the polymerization was stopped by cooling, degassing the reactor and introducing 1 ml of methanole. The achieved polymer was washed with acidic methanol, than with methanol and dried in an oven at 60° C. under vacuum.

The polymerization conditions and the characterization data of the polymer obtained are reported in Table 1.

Polymerization Example 7

The general procedure described in Ex. 1–6 was followed, except that the metallocene indicated in Table 1 were used and the polymerization was carried out in heptane (150 ml) instead of hexane and by using a 260 ml glass autoclave.

The polymerization conditions and the data relating to the obtained polymer are indicated in Table 1.

Polymerization Examples 8 and 9 (Comparison)

The general procedure described in Ex. 1–6 was followed, except that the metallocenes indicated in Table 1 were used.

The polymerization conditions and the data relating to the obtained polymer are indicated in Table 1.

Polymerization Examples 10 to 12
Ethylene Polymerization in a Steel Autoclave A 1 L steel autoclave, provided with magnetic stirrer, temperature indicator and feeding line for the monomers was purified and fluxed with ethylene at 80° C. At room temperature it was introduced 500 ml of hexane and 1 mmol of TIBAL as a scavenger. The catalytic system was prepared separately in a 10 ml schlenk tube by consecutively introducing MAO (10 wt % vol in toluene) and the metallocene solved in toluene (the lowest amount as possible). After 10 minutes of stirring the solution was injected into the autoclave through a vial by an ethylene overpressure, the temperature risen to 80° C. and pressurized with ethylene to a final pressure of 10 bar. The total pressure was kept constant by feeding ethylene. After 1 h the polymerization was stopped by cooling and introducing 1 bar of carbon monoxide. Then the reactor was degassed and the polymer was recovered by filtration and dried in an oven at 60° C. under vacuum.

The polymerization conditions and the data relating to the obtained polymer are indicated in Table 1.

Polymerization Examples 13 to 16
Ethylene/1-hexene Copolymerization

In a 260 ml glass autoclave, provided with magnetic stirrer, temperature indicator and feeding line for ethylene was purified and fluxed with ethylene at 35° C. At room temperature it was introduced heptane to reach the final volume and 1-hexene in the amounts as indicated in Table 2. The catalytic system was prepared separately in 10 ml of heptane by consecutively introducing the MAO and the metallocene solved in 3 ml of toluene. After 5 minutes of stirring the solution was introduced into the autoclave under ethylene flow. The reactor was closed, the temperature risen to 70° C. and pressurized to 4.5 bar. The total pressure was kept constant by feeding ethylene. After 15 minutes the polymerization was stopped by cooling, degassing the reactor and introducing 1 ml of methanol. The achieved polymer was washed with acidic methanol, then with methanol and dried in an oven at 60° C. under vacuum.

The polymerization conditions and the data relating to the obtained polymer are indicated in Tables 2 and 3.

Polymerization Examples 17 and 18 (Comparison)

The general procedure described in Ex. 13–16 was followed, except that the polymerization was carried out in a 200 ml glass autoclave and by using 100 ml as total liquid volume.

The polymerization conditions and the data relating to the obtained polymer are indicated in Tables 2 and 3.

Polymerization Examples 19 to 22 and 23 (Comparison)
Ethylene/Propylene Copolymerization Polymerizations were performed at 50° C., in a 250 mL glass reactor, equipped with a mechanical stirrer, a thermometer and a pipe for monomers feeding. 100 mL of toluene and the TIOAO solution, fresh prepared as above described (3.45 mmol of Aluminum) was introduced in the nitrogen-purged reactor, kept in a thermostatic bath. At the polymerization temperature, a ethene/propylene gaseous mixture (60 wt % of ethene) was fed and continuously discharged with a flow of 1.5 L/min and a pressure of 1.1 atm. After 2 minutes, 3.45 $\mu$mol of catalyst, dissolved in 5 mL of toluene in the presence of 34 $\mu$moles of TIOA, were added to start the polymerization. During the polymerization, the temperature was kept within ±0.2° C. The polymerization was stopped after 15 min by adding 1 mL of methanol and the copolymer was recovered by precipitation in methanol/HCl and filtration and finally dried at 50° C. under reduced pressure.

The polymerization conditions and the data relating to the obtained polymer are indicated in Table 4.

Polymerization Examples 24 to 27
Ethylene/Propylene/ENB Terpolymerization

Polymerizations were performed at 50° C., in a 250 mL glass reactor, equipped with a mechanical stirrer, a thermometer and a pipe for monomers feeding. 100 mL of toluene, 2 mL of ENB and 1.2 mL of MAO solution (2.0 mmol of Aluminum) were introduced in the nitrogen-purged reactor, kept in a thermostatic bath. At the polymerization temperature, a ethene/propylene gaseous mixture (60 wt % of ethene) was fed and continuously discharged with a flow of 1.5 L/min and a pressure of 1.1 bar. After 2 minutes 2.0 $\mu$mol of catalyst, dissolved in 5 mL of toluene in the presence of 20 $\mu$moles of MAO, were added to start the polymerization. During the polymerization, the temperature was kept within ±0.2° C. The polymerization was stopped after 15 min by adding 1 mL of methanol and the copolymer was recovered by precipitation in methanol/HCl and filtration and finally dried at 50° C. under reduced pressure. The polymerization conditions and the data relating to the obtained polymer are indicated in Table 5.

TABLE 1

(ethylene homopolymerization)

| Ex. | Zirconocene Type | (mg) | AlR$_3$ Type | (mmol) | Al/Zr (mol) | hexane (ml) | Time (min) | yield (g) | Activity (Kg/gZr.h) | I.V. (dL/g) |
|---|---|---|---|---|---|---|---|---|---|---|
| 1 | Z$_S$-51 | 0.4 | MAO | 2.3 | 3000 | 100 | 5 | 1.5 | 256.9 | 3.97 |
| 2 | Z$_S$-51 | 0.3 | TIOA—H$_2$O | 1.7 | 3000 | 100 | 20 | 0.09 | 5.1 | — |
| 3 | Z$_S$-0 | 0.1 | MAO | 0.22 | 1050 | 100 | 10 | 1.0 | 306.1 | 3.4 |
| 4 | Z$_S$-1 | 0.1 | MAO | 0.22 | 1060 | 100 | 8 | 1.65 | 663.0 | 4.0 |
| 5 | Z$_S$-3 | 0.08 | MAO | 0.16 | 1000 | 100 | 10 | 2.13 | 929.6 | >4.3 |
| 6 | Z$_S$-3 | 0.11 | MAO | 0.21 | 1060 | 100 | 2 | 1.0 | 1496.4 | — |
| 7 | Z$_S$-2 | 0.11 | MAO | 0.23 | 1080 | 150* | 15 | 5.8 | 1196.4 | 4.5 |
| 8 (comp.) | Z$_S$-50 | 0.5 | MAO | 1.2 | 1060 | 100 | 10 | 1.7 | 97.7 | 2.6 |
| 9 (comp.) | Z$_S$-50 | 0.5 | TIOA—H$_2$O | 1.16 | 1030 | 100 | 30 | 0.05 | 1.0 | — |
| 10 | Z$_S$-0 | 0.5 | MAO | 0.21 | 200 | 500 | 60 | 15.3 | 159.2 | 2.1 |
| 11 | Z$_S$-1 | 0.4 | MAO | 0.16 | 195 | 500 | 60 | 21.1 | 282.6 | 2.3 |
| 12 | Z$_S$-3 | 0.3 | MAO | 0.11 | 195 | 500 | 60 | 30.1 | 583.3 | 5.1 |

TABLE 2

(ethylene/1-hexene copolymerization)

| Ex. | Zirconocene Type | (mg) | AlR$_3$ Type | (mmol) | Al/Zr (mol) | 1-hexane (ml) | Time (min) | yield (g) | activity (Kg/gZr.h) | I.V. (dL/g) |
|---|---|---|---|---|---|---|---|---|---|---|
| 13 | Z$_S$-1 | 0.10 | MAO | 0.23 | 1000 | 10 | 15 | 1.89 | 404.9 | 1.12 |
| 14 | Z$_S$-3 | 0.11 | MAO | 0.22 | 1060 | 10 | 15 | 1.59 | 336.3 | 1.46 |
| 15 | Z$_S$-2 | 0.11 | MAO | 0.23 | 1080 | 5 | 15 | 3.48 | 713.8 | 1.71 |
| 16 | Z$_S$-2 | 0.11 | MAO | 0.23 | 1080 | 10 | 20 | 0.67 | 103.0 | 1.55 |
| 17 | Z$_S$-0 | 0.10 | MAO | 0.23 | 1070 | 2 | 10 | 2.36 | 736.9 | 1.62 |
| 18 (comp) | Z$_S$-50 | 0.50 | MAO | 1.20 | 1170 | 10 | 15 | 3.86 | 165.5 | 0.71 |

TABLE 3

(ethylene/1-hexene copolymerization)

| Ex | Zirconocene | 1-hexene (mol %) | Tm (° C.) | ΔH (J/g) | HHH | EHE | HHE | EHE/(EHE + HHE + HHH) | $r_1$ | $r_1$–$r_2$ |
|---|---|---|---|---|---|---|---|---|---|---|
| 13 | Z$_S$-1 | 11.6 | 72.5 | 40.2 | 9.94 | 0 | 1.71 | 0.85 | 9.58 | 0.531 |
| 14 | Z$_S$-3 | 11.5 | 74.5 | 33.5 | 8.89 | 0.38 | 2.20 | 0.77 | 10.48 | 1.086 |
| 15 | Z$_S$-2 | — | 100.3 | 90.5 | — | — | — | — | — | — |
| 16 | Z$_S$-2 | 6.7 | 93.5 | 60.9 | 5.99 | 0 | 0.74 | 0.89 | 17.5 | 0.686 |
| 17 | Z$_S$-0 | 4.3 | 106.0 | 108 | 4.16 | 0 | 0.14 | 0.96 | 7.35 | 0.363 |
| 18 (comp.) | Z$_S$-50 | 17.9 | 45* | 8* | 14.93 | 0.27 | 2.71 | 0.83 | 7.05 | 0.410 |

N.M.R (% mols)

*data from the first heating

TABLE 4

(ethylene/propylene copolymerization)

| Example | Zirconocene dichloride Type | (mg) | Al/Zr (mol) | Time (min) | Yield (g) | Activity (Kg/gZr.h) | C$_2$ (mol %) | I.V. (dL/g) | $r_1r_2$ |
|---|---|---|---|---|---|---|---|---|---|
| 19 | Z$_S$-1 | 1.7 | 1000 | 15 | 4.97 | 63.2 | 78.8 | 0.68 | 0.35 |
| 20 | Z$_S$-3 | 1.8 | 1000 | 15 | 5.9 | 74.8 | 72.2 | 1.17 | 0.69 |
| 21 | Z$_S$-2* | 0.9 | 2000 | 15 | 3.48 | 87.2 | 75.7 | 1.09 | 0.62 |
| 22 | Z$_S$-0 | 1.6 | 1000 | 15 | 2.86 | 36.4 | 79.1 | 0.60 | 0.39 |
| 23 (comp) | Z$_S$-50 | 1.4 | 1000 | 15 | 1.35 | 19.5 | 72.3 | 0.51 | 0.33 |

TABLE 5

(ethylene/propylene/ENB polymerization)

| Example | Zirconocene dichloride Type | (mg) | Al/Zr (mol) | Time (min) | Yield (g) | Activity (Kg/gZr.h) | I.V. (dL/g) | C$_2$ (mol %) | ENB (mol %) |
|---|---|---|---|---|---|---|---|---|---|
| 24 | Z$_S$-1 | 1.3 | 1000 | 15 | 3.45 | 57.6 | 0.37 | 72.5 | 13.0 |
| 25 | Z$_S$-3 | 1.4 | 1000 | 15 | 1.98 | 33.2 | n.d. | 77.8 | 12.5 |
| 26 | Z$_S$-2 | 1.3 | 1000 | 15 | 9.85 | 166.0 | 0.42 | 55.2 | 5.4 |
| 27 | Z$_S$-0 | 1.2 | 1000 | 15 | 1.35 | 22.8 | 0.35 | 72.3 | 15.5 | n.d. not determined

What is claimed is:

1. A process for the preparation of polymers of ethylene comprising the polymerization reaction of ethylene and optionally one or more olefins in the presence of a catalyst comprising the product obtained by contacting:

(A) a metallocene compound of formula (I):

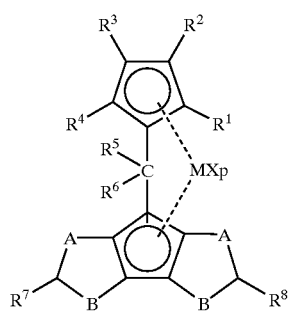

(I)

wherein
the rings containing A and B have a double bond in the allowed position having an aromatic character;

A and B are selected from sulfur (S), oxygen (O) or $CR^9$, $R^9$ being hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms belonging to groups 13 or 15–17 of the Periodic Table of the Elements, with the proviso that if A is S or O, B is $CR^9$ or if B is S or O, A is $CR^9$, and A and B cannot simultaneously be $CR^9$;

$R^1$, $R^2$, $R^3$, $R^4$, $R^5$, $R^6$, $R^7$, and $R^8$ which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms belonging to groups 13 or 15–17 of the Periodic Table of the Elements, and at least two adjacent substituents $R^1$ and $R^2$, $R^3$ and $R^4$, or $R^5$ and $R^6$ can form a ring comprising 4 to 8 atoms;

M is an atom of a transition metal selected from group 3, 4, 5, 6 or the lanthanide or actinide groups in the Periodic Table of the Elements;

X, which may be the same as or different from each other, is hydrogen, halogen atom, a $R^{10}$, $OR^{10}$, $OSO_2CF_3$, $OCOR^{10}$, $SR^{10}$, $NR^{10}{}_2$ or $PR^{10}{}_2$ group, wherein the substituents $R^{10}$ are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms belonging to groups 13 or 15–17 of the Periodic Table of the Elements;

p is an integer of from 1 to 3, being equal to the oxidation state of the metal M minus 2;

with the proviso that at least one of $R^7$ and $R^8$ is not hydrogen;

and (B) at least one member selected from the group consisting of an alumoxane and a compound of formula $D^+E^-$, wherein $D^+$ is a Brønsted acid, which gives a proton and reacts irreversibly with a substituent X of the metallocene of formula (I) and $E^-$ is a compatible anion, which stabilizes the active catalytic species originating from the reaction of the two compounds, and which is removed by an olefinic monomer.

2. The process according to claim 1, wherein in the metallocene compound of formula (I) the transition metal N is selected from the group consisting of titanium, zirconium and hafnium.

3. The process according to claim 1, wherein in the metallocene compound of formula (I) the X substituents are chlorine atoms or methyl groups.

4. The process according to claim 1, wherein in the metallocene compound of formula (I) A and B are sulfur or a CH group, and if A is a CH group, B is sulfur, or if B is a CH group, A is sulfur, $R^5$ and $R^6$ are $C_1$–$C_{20}$-alkyl groups, and $R^7$ is equal to $R^8$.

5. The process according to claim 4, where $R^1$, $R^3$ and $R^4$ are hydrogen, $R^5$ and $R^6$ are methyl, $R^2$ is $C_1$–$C_{20}$-alkyl groups and $R^7$ and $R^8$ are methyl groups.

6. The process according to claim 1, wherein said alumoxane is obtained by contacting water with an organo-aluminium compound of formula $H_jAlR^{12}{}_{3-j}$ or $H_jAl_2R^{12}{}_{6-j}$, where $R^{12}$ substituents, same or different, are hydrogen atoms, $C_1$–$C_{20}$-alkyl, $C_3$–$C_{20}$-cycloalkyl, $C_6$–$C_{20}$-aryl, $C_7$–$C_{20}$-alkylaryl or $C_7$–$C_{20}$-arylalkyl, optionally containing silicon or germanium atoms, and j ranges from 0 to 1, being also a non-integer number.

7. The process according to claim 6, wherein said alumoxane is methylalumoxane (MAO), tetra-(isobutyl) alumoxane (TIBAO), tetra-(2,4,4-trimethyl-pentyl) alumoxane (TIOAO), tetra-(2,3-dimethylbutyl)alumoxane (TDMBAO) or tetra-(2,3,3-trimethylbutyl)alumoxane (TTMBAO).

8. The process according to claim 1, wherein the anion $E^-$ comprises one or more boron atoms.

9. The process according to claim 1, wherein the process is carried out in the presence of an alpha-olefin selected from the group consisting of propylene, 1-butene, 1-pentene, 1-hexene, 4-methyl-1-pentene, 1-octene, 1-decene and 1-dodecene.

10. The process according to claim 9, wherein said alpha-olefin is 1-hexene or propylene.

11. The process according to claim 9, wherein the molar content of alpha-olefin derived units is between 0% and 60%.

12. The process according to claim 1, wherein the process is carried out in the presence of a cyclic monomer.

13. The process according to claim 12, wherein the cyclic comonomer is 5-ethyliden-2-norbornene.

14. The process according to claim 12, wherein the molar content of the cyclic monomer is between 0 mol % and 30 mol %.

15. A metallocene compound of formula (I):

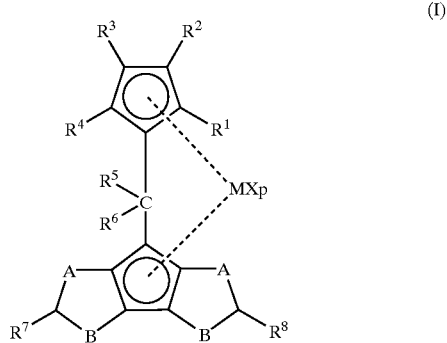

(I)

wherein
A and B are selected from sulfur (S), oxygen (O) or $CR^9$, $R^9$ being hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms belonging to groups 13 or 15–17 of the Periodic Table of the Elements, with the proviso that if A is S or O, B is $CR^9$ or if B is S or O, A is $CR^9$, and A and B cannot simultaneously be $CR^9$;

$R^1$, $R^2$, $R^3$, $R^4$, $R^5$, $R^6$, $R^7$, and $R^8$ which may be the same as or different from each other, are hydrogen, a $C_0$–$C_{20}$-alkyl, $C_3$–$C_{20}$-cycloalkyl, $C_2$–$C_{20}$-alkenyl, $C_6$–$C_{20}$-aryl, $C_3$–$C_{20}$-alkylaryl, or $C_7$–$C_{20}$-arylalkyl radical, optionally containing heteroatoms belonging to groups 13 or 15–17 of the Periodic Table of the Elements, and at least two adjacent substituents $R^1$ and $R^2$, $R^3$ and $R^4$, or $R^5$ and $R^6$ can form a ring comprising 4 to 8 atoms M is an atom of a transition metal from group 3, 4, 5, 6 or the lanthanide or actinide groups in the Periodic Table of the Elements, X, which may be the same as or different from each other, is hydrogen, halogen atom, a $R^{10}$, $OR^{10}$, $OSO_2CF_3$, $OCOR^{10}$, $SR^{10}$, $NR^{10}_2$ or $PR^{10}_2$ group, wherein the substituents $R^{10}$ are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms belonging to groups 13 or 15–17 of the Periodic Table of the Elements;

p is an integer of from 1 to 3, being equal to the oxidation state of the metal M minus 2;

and wherein the rings containing A and B have a double bond in the allowed position having an aromatic character; and with the proviso that at least one of $R^7$ and $R^8$ is not hydrogen.

16. A ligand of formula (II):

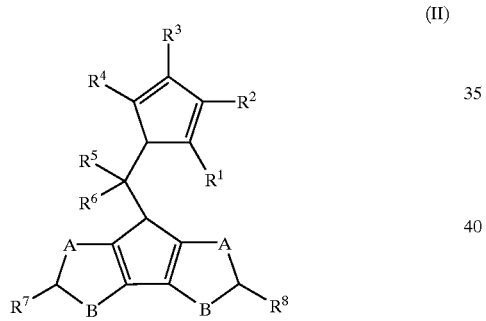

(II)

or its double bond isomers,
wherein the rings containing A and B have double bonds in any of the allowed positions, having an aromatic character and A and B are selected from sulfur (S), oxygen (O) or $CR^9$, $R^9$ being hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms belonging to groups 13 or 15–17 of the Periodic Table of the Elements, with the proviso that if A is S or O, B is $CR^9$ or if B is S or O, A is $CR^9$, and A and B cannot simultaneously be $CR^9$;

$R^1$, $R^2$, $R^3$, $R^4$, $R^5$, $R^6$, $R^7$, and $R^8$ which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms belonging to groups 13 or 15–17 of the Periodic Table of the Elements, and at least two adjacent substituents $R^1$ and $R^2$, $R^3$ and $R^4$, or $R^5$ and $R^6$ can form a ring comprising 4 to 8 atoms; with the proviso that at least one of $R^7$ and $R^8$ is not hydrogen.

17. A process for preparing the compound of formula (VII)

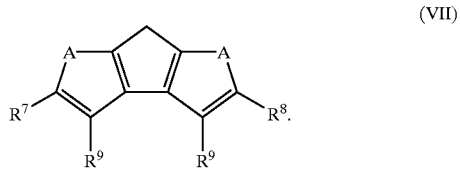

(VII)

wherein A is sulfur (S) or oxygen (O), $R^9$ is hydrogen, a $C_1$–$C_{20}$-alkyl, $C_1$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms belonging to groups 13 or 15–17 of the Periodic Table of the Elements;

$R^7$ and $R^8$ which may be the same as or different from each other, are a $C_1$–$C_{20}$-alkyl, $C_3$–$C_{20}$-Cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms belonging to groups 13 or 15–17 of the Periodic Table of the Elements;

comprising the following steps:

i) contacting an equimolar mixture of compounds of formulae (XI) and (XII):

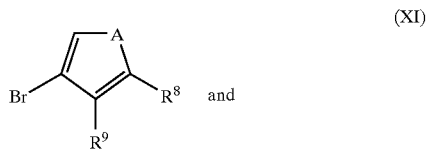

(XI)

and

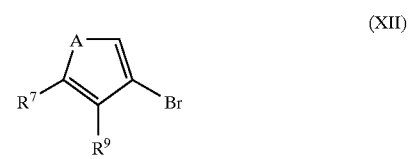

(XII)

wherein A is sulfur or oxygen,
with a Lewis acid or a mixture of a Lewis acid and a protonic acid;

ii) treating the thus obtained product from step i) with $CH_2O$ in a molar ratio between said mixture and $CH_2O$ of a range between 10:1 and 1:10;

iii) contacting the thus obtained product from step ii) with a compound selected from an organolithium compound, sodium or potassium; and iv) contacting the thus obtained product from step iii) with an agent selected from the group consisting of copper (II) chloride, iodine and Mg/Pd, in order to obtain a compound of general formula (VII).

18. The process according to claim 17, wherein the Lewis acid is selected from the group consisting of zinc dichloride, cadmium dichloride, mercury dichloride, tin tetrachloride, trifluoroborane, zirconium tetrachloride, and titanium tetrachloride.

19. A process for preparing the compound of formula (VII)

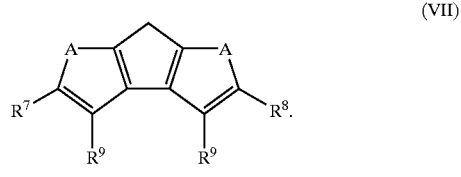
(VII)

wherein A is sulfur (S) or oxygen (O), $R^9$ is hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms belonging to groups 13 or 15–17 of the Periodic Table of the Elements;

$R^7$ and $R^8$ which may be the same as or different: from each other, are a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms belonging to groups 13 or 15–17 of the Periodic Table of the Elements;

comprising the following steps:

i) contacting a compound of formula (XIII):

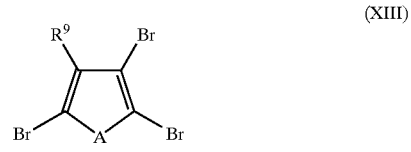
(XIII)

with a base selected from an organolithium compound, sodium or potassium; treating with a formic ester, wherein the molar ratio between said ester and the compound of formula (XIII) is at least 1:2, and subsequently treating the obtained product with a reducing agent in order to obtain a compound of formula (XIV):

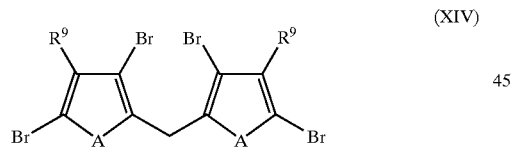
(XIV)

ii) contacting the compound of formula (XIV) with a base selected from an organolithium compound, sodium or potassium and subsequently treating the dimetallated compound with an alkylating agent to obtain the compound of formula (XV);

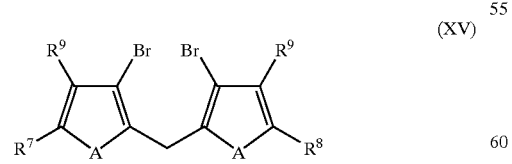
(XV)

and iii) contacting the alkylated compound obtained by step ii) with a coupling agent selected from the group consisting of copper (II) chloride, iodine and Mg/Pd in order to obtain the compound of formula (VII).

20. A process for preparing the compound of formula (VII)

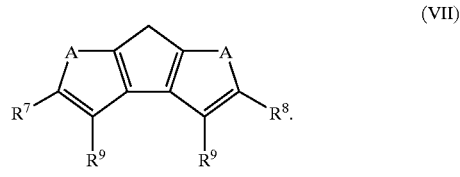
(VII)

wherein A is sulfur (S) or oxygen (O), $R^9$ is hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms belonging to groups 13 or 15–17 of the Periodic Table of the Elements;

$R^7$ and $R^8$ which may be the same as or different from each other, are a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms belonging to groups 13 or 15–17 of the Periodic Table of the Elements;

comprising the following steps:

i) contacting a compound of formula (XIII):

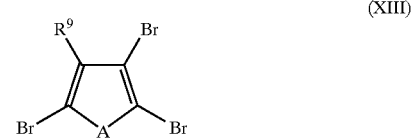
(XIII)

with a base selected from an organolithium compound, sodium or potassium; treating with a formic ester, wherein the molar ratio between said ester and the compound of formula (XIII) is at least 1:2, and subsequently treating the obtained product with a reducing agent in order to obtain a compound of formula (XIV):

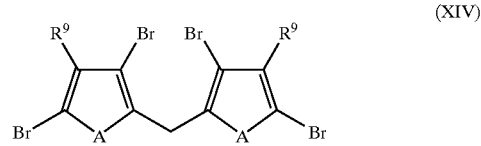
(XIV)

ii) contacting the compound of formula (XIV) with a base selected from an organolithium compound, sodium or potassium and subsequently treating the dimetallated compound with an ester of boric acid and a proconating agent in order to obtain the compound of formula (XVI);

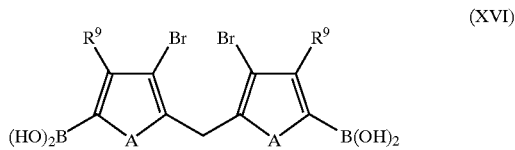
(XVI)

and subsequently contacting with a mixture of an alkylating agent in the presence of an transition metal complex compound for obtaining the compound of formula (XV);

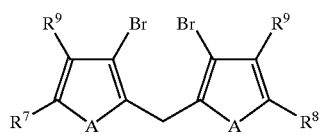
(XV)
and
iii) contacting the alkylated compound obtained by step ii) with a coupling agent selected from the group consisting of copper (II) chloride, iodine and Mg/Pd in order to obtain the compound of formula (VII).
* * * * *

UNITED STATES PATENT AND TRADEMARK OFFICE
CERTIFICATE OF CORRECTION

PATENT NO. : 6,864,333 B2
DATED : March 8, 2005
INVENTOR(S) : Tiziano Dall'Occo et al.

It is certified that error appears in the above-identified patent and that said Letters Patent is hereby corrected as shown below:

Column 47,
Lines 4 and 5, change "$C_0$-$C_{20}$-alkyl," to -- $C_1$-$C_{20}$-alkyl, --

Columj 48,
Line 15, change "$C_1$-$C_{20}$-cycloalkyl" to -- $C_3$-$C_{20}$-cycloalkyl --

Signed and Sealed this

Thirty-first Day of May, 2005

JON W. DUDAS
*Director of the United States Patent and Trademark Office*